US010239923B2

(12) United States Patent
Willbold et al.

(10) Patent No.: US 10,239,923 B2
(45) Date of Patent: Mar. 26, 2019

(54) SPECIFIC AMYLOID BETA BINDING PEPTIDES AND THE USE OF SAME FOR TREATING AND DIAGNOSING ALZHEIMER'S DEMENTIA

(71) Applicant: Forschungszentrum Juelich GmbH, Juelich (DE)

(72) Inventors: Dieter Willbold, Juelich (DE); Stephan Rudolph, Juelich (DE); Janine Kutzsche, Dueren (DE); Susanne Aileen Funke, Sonnefeld (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 15/559,078

(22) PCT Filed: Mar. 1, 2016

(86) PCT No.: PCT/DE2016/000091
§ 371 (c)(1),
(2) Date: Sep. 18, 2017

(87) PCT Pub. No.: WO2016/150416
PCT Pub. Date: Sep. 29, 2016

(65) Prior Publication Data
US 2018/0072786 A1    Mar. 15, 2018

(30) Foreign Application Priority Data
Mar. 20, 2015   (DE) .................. 10 2015 003 503

(51) Int. Cl.
*C07K 7/08*     (2006.01)
*C07K 7/64*     (2006.01)
*A61K 38/00*    (2006.01)
*A61K 38/10*    (2006.01)
*C07K 14/47*    (2006.01)

(52) U.S. Cl.
CPC .......... *C07K 14/4711* (2013.01); *A61K 38/10* (2013.01); *C07K 7/08* (2013.01); *C07K 7/64* (2013.01); *A61K 38/00* (2013.01); *C07K 14/4713* (2013.01); *G01N 2333/4709* (2013.01); *G01N 2800/2821* (2013.01)

(58) Field of Classification Search
CPC ........ C07K 7/08; C07K 7/64; C07K 14/4711; C07K 14/4713; A61K 38/10; G01N 2333/4709; G01N 2800/2821
See application file for complete search history.

(56) References Cited

U.S. PATENT DOCUMENTS 7,384,910 B2 * 6/2008 Castillo .................. A61K 38/08
                                                        514/17.8
2007/0093415 A1   4/2007 Martin
2008/0058219 A1   3/2008 Lockhart et al.
2015/0307552 A1  10/2015 Willbold et al.

FOREIGN PATENT DOCUMENTS

DE    102005049537 A1    4/2007
WO    WO 02081505 A2    10/2002
WO    WO 2014041115 A2   3/2014

OTHER PUBLICATIONS

Wiesehan K et al. Selection of D-amino-acid peptides that bind to Alzheimer's disease amyloid peptide Abeta1-42 by mirror image phage display. ChemBioChem. 4, 748-753. (Year: 2003).*
Ton N. M. Schumacher, et al.,Identification of D-Peptide Ligands Through Mirror-Image Phage Display, Science, vol. 271, Mar. 29, 1996, pp. 1854-1857.
Thomas Van Groen et al: "Reduction of Alheimer's Disease Amyloid Plaque Load in Transgenic Mice by D3, a D-Enantiomeric Peptide Identified by Mirror Image Phage Display", Chemmedchem, vol. 3, No. 12, Dec. 15, 2008 (Dec. 15, 2008), pp. 1848-1852, XP055239322.
Christian Haass, et al., "Cellular Processing of β-Amyloid Precursor Protein and the Genesis of Amyloid β-Peptide", Cell, vol. 75, Dec. 17, 1993, pp. 1039-1042.
Saul B. Needleman, et al., "A General Method Applicable to the Search for Similarities in the Amino Acid Sequence of Two Proteins", J. Mol. Biol. vol. 48, Dec. 1970, pp. 443-453.
Daniela Puzzo, et al., "Amyloid-β Peptide: Dr. Jekyll or Mr. Hyde?", J. Alzheimers Dis. vol. 33(01), Jun. 30, 2013, pp. 1-14.
Temple F. Smith, et al., "Comparison of Biosequences", Advances in Applied Mathematics, vol. 2, Dec. 1981, pp. 482-489.
Rudolph S et al: "Characterization of D-Enantiomeric Peptides Binding to Monomeric Amyloid Beta (1-42) Identified by a Competitive Mirror Image Phage Display", Alzheimer's & Dementia, vol. 10, No. 4, p. 1-424, Jul. 1, 2014 (Jul. 1, 2014), p. 469, XP002757151.
Schwarzman Alexander L et al: "Selection of peptides binding to the amyloid b-protein reveals potential inhibitors of amyloid formation.", Amyloid: The International Journal of Experimental and Clinical Investigation: The Official Journal of The International Society of Amyloidosis Dec. 2005, vol. 12, No. 4, Dec. 2005 (Dec. 2005), pp. 199-209, XP009189838.
Brendan P. Orner et al: "Phage Display Affords Peptides that Modulate [bet]-Amyloid Aggregation", Journal of The American Chemical Society, vol. 128, No. 36, Mar. 22, 2006 (Mar. 22, 2006), pp. 11882-11889, XP055269482.
Susanne Aileen Funke et al: "Mirror image phage display-a method to generate d-peptide ligands for use in diagnostic or therapeutical applications", Molecular Biosystems, vol. 5, No. 8, Jan. 1, 2009 (Jan. 1, 2009), pp. 783, XP055069250.
Silke Hoffmann et al: "Competitively selected protein ligands pay their increase in specificity by a decrease in affinity", Molecular Biosystems, vol. 6, No. 1, Jan. 1, 2010 (Jan. 1, 2010), p. 126, XP055027668.

(Continued)

*Primary Examiner* — Kimberly Ballard
(74) *Attorney, Agent, or Firm* — Leydig, Voit & Mayer, Ltd.

(57) ABSTRACT

Peptides specifically binding amyloid beta and to methods of treating and diagnosing Alzheimer's dementia using such peptides are provided.

15 Claims, 9 Drawing Sheets
Specification includes a Sequence Listing.

(56) References Cited

OTHER PUBLICATIONS

Katja Wiesehan et al: "Mirror-image Phage Display: Aiming at the Mirror", Chembiochem—A European Journal of Chemical Biology., vol. 4, No. 9, Sep. 4, 2003 (Sep. 4, 2003), pp. 811-815, XP055269590.
Stephan Rudolph et al: "Competitive Mirror Image Phage Display Derived Peptide Modulates Amyloid Beta Aggregation and Toxicity", Plos One, vol. 11, No. 2, Feb. 3, 2016 (Feb. 3, 2016), pp. e0147470, XP055269486.

* cited by examiner

SPECIFIC AMYLOID BETA BINDING PEPTIDES AND THE USE OF SAME FOR TREATING AND DIAGNOSING ALZHEIMER'S DEMENTIA

CROSS-REFERENCE TO PRIOR APPLICATIONS

This application is a U.S. National Phase application under 35 U.S.C. § 371 of International Application No. PCT/DE2016/000091, filed on Mar. 1, 2016, and claims benefit to German Patent Application No. DE 10 2015 003 503.7, filed on Mar. 20, 2015. The International Application was published in German on Sep. 29, 2016 as WO 2016/150416 A1 under PCT Article 21(2).

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 4,787 bytes ASCII (Text) file named "815925SequenceListing_ST25," created Sep. 6, 2017.

FIELD

The invention relates to peptides specifically binding amyloid beta and to the use of same for treating and diagnosing Alzheimer's dementia.

BACKGROUND

The D-enantiomeric peptide with the name "D3" is known from WO 02/081505 A2. It was identified by a mirror-image phage display selection against predominantly monomeric Aβ(1-42) with the plan to stabilize this by the binding and to prevent conversion thereof into toxic Aβ aggregates. Based on the current understanding, D3 preferably converts the particularly toxic Aβ oligomers into non-toxic, non-amyloidogenic and ThT-negative, amorphous aggregates. In the animal model, even with oral administration of D3 in drinking water, treated transgenic AD mice contained much fewer plaques and demonstrated significantly improved cognitive capabilities.

However, there is still no approved medicinal drug available for the causal treatment of Alzheimer's dementia (AD). Deposits of what are known as beta amyloid peptides (Aβ) in the form of plaques are typically found in the brains of AD patients post mortem. Various forms of the Aβ, for example fibrils, have therefore long been blamed for the development and progression of AD.

For some years, the small, freely diffusible Aβ oligomers in particular have been considered to be the main cause of the development and progression of AD.

Monomeric Aβ is constantly produced throughout our entire life in our body by sequential proteolysis of the precursor protein APP (amyloid precursor protein) by β and γ-secretases (Haass and Selkoe 1993) and is not toxic per se. There are even increasing suggestions that monomeric Aβ has a physiological, perhaps even neuroprotective function in the brain (Puzzo and Arancio 2013).

It is speculated whether Aβ monomers randomly amalgamate depending on their concentration (which is determined ultimately by formation and breakdown rates in the body) and thus are increasingly likely to amalgamate spontaneously to form Aβ oligomers with increasing age. Once formed, Aβ oligomers might then multiply by a prion-like mechanism and could ultimately lead to the disease.

On the basis of these considerations, the objective of causal treatment should be to prevent the formation of toxic Aβ oligomers or to completely eliminate oligomers already present and/or to prevent the prion-like multiplication thereof, moreover without reducing the Aβ monomer concentration.

There is thus currently no causally acting medicinal drug for the treatment of Alzheimer's dementia. Used medicinal drugs are at best capable of alleviating some symptoms, but cannot delay progression of the disease, let alone stop it.

There are indeed some substances available which reduce the concentration of Aβ monomers in a wide range of ways, for example by gamma-secretase modulators, Aβ-binding ligands, etc. However, since a physiological, perhaps even neuroprotective function of monomeric Aβ in the brain is postulated, on the basis of the most recent findings in relation to the mechanism of action of Alzheimer's dementia it is not considered to be a promising approach to reduce the Aβ concentration of the monomers, but instead the concentration of the Aβ oligomers.

This hypothesis has also been confirmed by the previous negative results of clinical studies (phases II and III) on humans with active substances that reduce the monomer concentration.

SUMMARY

In an embodiment, the present invention provides a peptide specifically binding an amyloid beta species, said peptide comprising at least one amino acid sequence selected from the group consisting of SEQ ID NO: 1, SEQ ID NO: 2, SEQ ID NO: 3, SEQ ID 4, SEQ ID NO: 5, SEQ ID NO: 6, SEQ ID NO: 7, SEQ ID NO: 8, SEQ ID NO: 9, SEQ ID NO. 10, SEQ ID NO. 11, SEQ ID NO. 12, SEQ ID NO. 13, SEQ ID NO: 14, SEQ ID NO: 15, SEQ ID NO: 16, SEQ ID NO: 17, SEQ ID NO: 18, SEQ ID NO: 19, SEQ ID NO: 20 and/or SEQ ID NO: 21 and also homologues, fragments and parts thereof and polymers of SEQ ID NO: 1, SEQ ID NO: 2, SEQ ID NO: 3, SEQ ID 4, SEQ ID NO: 5, SEQ ID NO: 6, SEQ ID NO: 7, SEQ ID NO: 8, SEQ ID NO: 9, SEQ ID NO. 10, SEQ ID NO. 11, SEQ ID NO. 12, SEQ ID NO. 13, SEQ ID NO: 14, SEQ ID NO: 15, SEQ ID NO: 16, SEQ ID NO: 17, SEQ ID NO: 18, SEQ ID NO: 19, SEQ ID NO: 20 and/or SEQ ID NO: 21.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
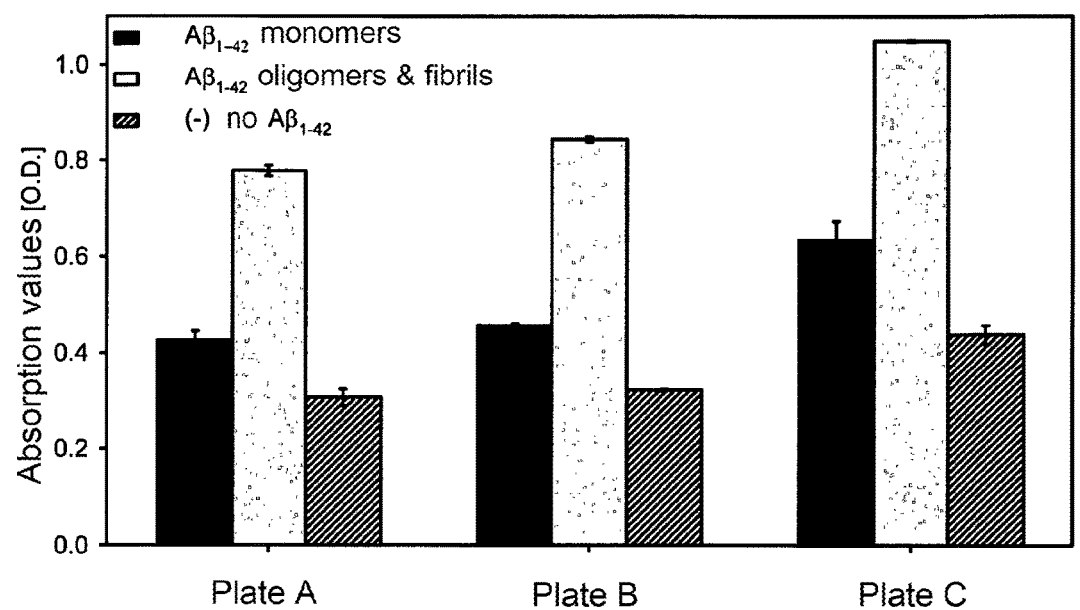
FIG. 1: shows an immobilization control of different $A\beta_{1-42}$ species.

Aspects of the invention provide:
A) peptides for the causal treatment of Alzheimer's disease by prevention of the formation of toxic amyloid β (Aβ) oligomers or aggregates or by detoxification thereof,
B) modification of the mirror-image phage display method, and/or
C) possibilities for use of the peptides according to the invention.

Ligands or peptides which specifically bind to certain A beta species are provided. In particular, peptides which bind more specifically to Aβ$_{1-42}$ monomer than to oligomeric and/or fibrillar Aβ$_{1-42}$ are provided.

Hereinafter, the terms 'target molecule' and 'bait' are used synonymously.

Here, the specificity, often also referred to as selectivity, means the following: If the ligand or peptide according to the invention under consideration binds two different molecules, which for example are referred to as a 'bait' and 'competitor', each binding pair, i.e. ligand-bait and ligand-competitor, can then be assigned a dissociation constant ($K_D$) or an association constant ($K_A=1/K_D$), on the assumption of a 1:1 binding model. The higher is the $K_A$ value, the greater is the affinity of the bond in question. The specificity of the ligand for the bait compared to the competitor is expressed by the greatest possible quotient of the affinities to the bait and the competitor. Ligands according to the invention have a quotient of the $K_A$ values of the ligand to the bait and to the competitor that is all the greater, the higher is the specificity.

In this sense, reference is made to relative specificity if the quotient of the $K_A$ values of the ligand, or peptide, to species A (bait) and of the ligand to species B (competitor) is at least greater than 1, preferably greater than 1.2, or 1.5, preferably greater than 2, 3, 4, 5, 6, 7, 8 or 9, in particular 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99, in particular 100, wherein the various A beta species, such as monomers, oligomers and fibrils, can be assumed as species A and species B.

Here, any intermediate value can be assumed. A rounding of the numerical values leads to the above-mentioned numerical values.

The model can be extended in principle to a number of competitors, which can be considered individually or in a mixture, even if the latter is not particularly elegant.

This problem is addressed in particular by peptides, specifically binding amyloid beta species, for treating Alzheimer's dementia. The specificity, often also referred to as selectivity, means here that the ligand or peptide according to the invention in principle can bind various A beta species, for example A beta monomer or A beta oligomer, or A beta fibrils. Each binding pair (for example ligand to A beta monomer and ligand to A beta oligomer and ligand to A beta fibrils) is assigned a dissociation constant ($K_D$) or an association constant ($K_A=1/K_D$), on the assumption of a 1:1 binding model. The higher is the $K_A$ value, the greater is the affinity of the bond in question.

The specificity of the ligand for the bait compared to the competitor is expressed by the greatest possible quotient of the affinities to the A beta monomer and to the A beta oligomer or A beta fibrils.

In accordance with certain embodiments of the invention, quotients of the $K_A$ values of the ligand to the A beta monomer and to the A beta oligomer (or A beta fibrils) are thus formed in order to determine the specificity. The greater is the quotient, the greater is the specificity.

The specificity or selectivity should not be confused here with the affinity, which results from the binding strength of ligands to one of the species. If various ligands are competing for the same target molecule, the less specific or selective ligand can thus have the greater binding affinity. In accordance with certain embodiments of the invention, the ligand which binds particularly specifically to a species such as monomer or oligomer or fibrils is the ligand that is identified. The biomolecules should be suitable as therapeutic agents and medicaments. The ligands or peptides obtained in this way have the desired properties.

With the aid of an optimized mirror-image phage display selection, peptides that for example bind more specifically to monomeric Aβ(1-42) than to oligomeric or fibrillar Aβ(1-42) were selected.

In order to identify peptides as ligands that bind as specifically as possible to monomeric A beta, but at the same time are as non-specific as possible for A beta oligomers and/or fibrils, a mirror-image phage display was developed and applied, in which there is a positive selection pressure for the monomer binding and a negative selection pressure for the binding to oligomers and fibrils.

In addition, due to the alternating use of different surface materials and/or due to the alternating use and non-use of blocking reagents, it was ensured that no surface combination was used twice, so as to avoid an enrichment of ligands which demonstrate a high affinity for the surface material.

Within the scope of certain embodiments of the invention it was found that the mirror-image phage display according to the prior art also leads, disadvantageously, to surface or blocking reagent-binding ligands, or at least to ligands that have bonded both to the surface and to the bait.

It should be noted that the method for mirror-image phage display, besides the selection of specific monomer binders as stated here, can of course also be used to find specific oligomer binders or even to find ligands vis-á-vis other species occurring in proteopathy.

In particular D-peptides which have one or more of the desired properties are identified by the selection method according to the invention.

The properties are, amongst other things, the binding specificity for A beta monomers, the inhibition of A beta fibril formation, the inhibition of A beta cytotoxicity, the elimination of A beta oligomers, and the conversion of A beta oligomers into non-toxic, non-amyloid species.

By optimizing the mirror-image phage display with competition against the aggregated Aβ1-42 species (Aβ1-42 oligomers, fibrils and high-molecular aggregates), ligands or peptides specifically binding A beta monomer for example are identified. If A beta oligomers are used as bait, specific ligands for A beta oligomers can thus be identified with a competition with A beta monomers.

In mirror-image phage display, a recombinant library of randomized peptide sequences for example, presented at the gp3 protein of the M13 phage and coded in the genome thereof, against the exact mirror image (D-enantiomer) of a naturally occurring L-enantiomeric target molecule (for example Aβ1-42) is selected.

The peptide sequence is advantageously presented at the N-terminus of the gp3 protein of the M13 phage and is present coded in the genome thereof.

The gp3 molecule, also referred to as gene product 3, is a protein which sits in the sheath of the phage and is required for the contact with the host cell.

The DNA sequence of the p3 gene of a selected phage contains the genetic information regarding the corresponding peptide sequence at the gp3 molecule and can be sequenced. After the sequencing, the genomic sequence can be transcribed into an amino acid sequence and can be synthesized as D-enantiomeric peptide, which binds to the physiological L-enantiomeric form of the target molecule (for example Aβ1-42).

What are known as panning rounds can be performed, for example six rounds. Here, the phage library is brought into contact with a fixed target molecule, also referred to as bait, and binding phages are isolated from the billionfold background of other, non-binding phages.

By way of example, the amount of phages that preferably bind to oligomeric or fibrillar species of Aβ1-42 is reduced by adding precisely these species as counterselectants or competitors, for example from the second panning round. Phages which demonstrate an increased affinity to Aβ1-42 oligomers and fibrils can thus be removed from the phage pool, so that for example Aβ1-42 monomer specific phages become enriched. The method can of course be adapted similarly to identify ligands and peptides specifically binding A beta oligomer.

In order to reduce an enrichment of phages having an affinity to plastics, BSA or streptavidin, differently treated surfaces are additionally used in accordance with the invention preferably in all panning rounds, and a further competitive step, for example with biotin, which binds with high affinity to streptavidin, is used. The selection pressure is increased successively in the following selection rounds. For this purpose, whilst the concentration of a biotinylated target molecule (for example monomeric D-enantiomeric Aβ1-42) remained stable, continuously higher concentrations of the non-biotinylated competitors acting as counterselectants, (for example D-enantiomeric Aβ1-42 oligomers and Aβ1-42 fibrils) were provided from the 2nd selection round.

Furthermore, in each round of the mirror-image phage display, another substrate surface was offered. This can be provided for example by different plastics species, such as polystyrene, polypropylene and polycarbonate.

By way of example, a choice can be made between a BSA-blocked polystyrene surface in round 1, a polypropylene surface in round 2, a BSA-blocked polycarbonate surface in round 3, a polystyrene surface in round 4, a BSA-blocked polypropylene surface in round 5, and a polycarbonate surface in round R6.

Blocking steps with, for example, 1% BSA in TBST can be performed for an hour at room temperature prior to the immobilization of the target peptide and for example only in rounds 1, 3 and 5, optionally further rounds.

The change between different substrates and alternating blocking and non-blocking of the surface increases the specificity for the target molecule or the bait in respect of the surface. In addition, besides the competition with closely related competitors, there is also a reduction of the ligands which bind non-specifically to plastics surfaces or BSA (blocking step).

The competitors and target molecules or bait are brought into contact simultaneously with the library. The method is thus characterized by the following steps:
a) providing an immobilized bait on a substrate.
b) bringing the immobilized molecule acting as bait into contact with a solution containing a library of molecules.
c) bringing the immobilized bait occupied by the molecules into contact with at least one competitor as specificity washing step.
d) separating and multiplying molecules still bound to the bait once the immobilized bait occupied by the molecules has been brought into contact with competitors.
e) repeating the aforementioned steps, wherein a different substrate is used with each repetition.
f) identifying the structure of the molecules remaining on the bait following the repetition.

A different substrate is used for example by changing the substrate type and/or by the blocking or non-blocking thereof by means of reagents.

A molecule from the group consisting of proteins, peptides, RNA, DNA, mRNA and chemical compounds is used as bait. In particular, various A beta species are used as bait.

For example, a component from the group consisting of microtiter plates, magnetic particles, and agarose or Sepharose beads is used as surface on which the bait is immobilized.

A mixture with at least one component from the group consisting of peptides, proteins, RNA, DNA and mRNA is preferably used as competitor. Here, competitors are bait-like molecules of which the binding points have similarities with those of the immobilized bait. In particular, the A beta species which are not used as bait are used as competitors.

The library and competitors are preferably brought into contact at the same time as the immobilized bait.

The method can be characterized in that the immobile phase during the specificity washing step is rinsed with a solution containing competitors.

The method can be characterized in that, during the specificity washing step, the solution with the library of molecules is swapped for a solution containing competitors.

The method can be characterized in that a solution with competitors is added to the immobile phase during the specificity washing step.

The specificity washing step and the addition of the library of molecules occur almost simultaneously. Should phages in principle have an affinity to A beta monomers and oligomers as bait and competitors, there is the possibility to bind to both targets simultaneously, and not successively. This advantageously results in the fact that only the ligands, which also preferably bind to the bait even with simultaneous exposure of bait and competitor, are enriched.

The concentration of competitors is preferably increased each selection round.

The bait according to point a) is thus a compound to which the biomolecule to be selected is to be bound. In accordance with methods known from the prior art, it is fixed to a first surface. By way of example (although this is not limiting), proteins, peptides, RNA or DNA molecules can be cited as bait, in particular A beta monomer. By way of example, microtiter plates, magnetic particles, and agarose or Sepharose beads can be used as potential surfaces.

In the second step b), the immobilized bait is brought into contact with a randomized library of molecules (especially biomolecules). These biomolecules compete for the binding to the bait. The randomized library is a mixture of a very large number, for example $10^{12}$, but also $10^4$ or only 100 different molecules in a mixture. A library of this type can consist for example of peptides, proteins, DNA, RNA or mRNA, which in each case are/is bound to specific vehicles and which can bind to bait. By way of example, phages, polysomes or bacterial surfaces can be considered as vehicles. The library can consist of artificial constituents or constituents isolated from nature, or can consist of a mixture of both. The term 'artificial' is understood to mean compounds produced from oligonucleotide synthesis, for example.

In accordance with certain embodiments of the invention, the immobilized bait occupied by biomolecules is brought into contact with competitors in step c). For this purpose, a specificity washing step is performed in step c), in which competitors are added to the solution or the immobile phase is rinsed with a solution containing competitors, or the solution with the library of molecules is swapped, preferably repeatedly, for a solution containing competitors. The competitors are bait-like molecules of which the binding points have similarities with those of the immobilized bait. The competitors present in solution compete in the washing step for the library molecules already bound to the immobilized bait. The library molecules that are similar to the library member that is actually "best" for the immobilized bait, but that bind better to one of the free competitors are thus withdrawn again from the immobilized bait. The speed of the detachment reaction of the binding library molecules is determined here primarily by the different disassociation constants ($k_{off}$ values) of the individual molecules. Molecules with a small $k_{off}$ value remain bound for the longest to the immobilized bait (as considered statistically) and thus have a lower statistical probability of being able to establish a bond to the offered competitor molecules. Such library molecules ultimately demonstrate a specific or selective binding to the bait. By way of example (although not limiting), proteins, peptides, DNA or RNA can be mentioned as competitors. The liquid containing the competitors is preferably aqueous and can contain a pH buffer.

Further optional components of the solution for the specificity washing step are salts, detergents or reducing agents.

The separation in step d) is performed for example by elution of phages from the bait so as to be able to multiply them. The phages contain the peptides.

During the subsequent multiplication of the library molecules still remaining on the bait after the specificity washing step according to step d), the bound biomolecules are separated from the bait and are multiplied by known methods. For this purpose, phage particles obtained by way of example after steps a) to c) are introduced into cells and multiplied. The separation can be performed by way of example by changing the pH value, heating, or changing (in particular increasing) the salt concentration.

In step e) the concentration of the selected biomolecules in the solution supplied to the bait after step a) is increased.

Preferably, 3 to 6 selection rounds, which contain steps a) to e), are performed. However, 1→10 or 1→20 repetitions can also be performed. The increase of the competitor concentration preferably performed here in step c) also leads to an improved selection with increasing cycle number. The concentration of the competitors can initially lie for example at 1 nmol/l. The change in concentration of the competitors can occur in steps of doubling or in steps of tenfold increases or more. Typical end concentrations lie at 1 µmol/l.

These ligands specifically binding to a bait are molecules which have an increased selectivity in respect of a specific bait, that is to say bind more specifically, but not necessarily more strongly, to a certain bait than to the bait of similar bait molecules. The ligands preferably bind exclusively to a certain bait. In the presence of competing molecules, the ligand or the peptide selected by the method will bind preferably to the target molecule.

A particularly relevant mirror-image phage display provides N-terminal biotinylated D-enantiomeric A beta$_{1-42}$ monomer in step a), a recombinant phage library in step b), and D-enantiomeric A beta$_{1-42}$ oligomers and/or D-enantiomeric A beta$_{1-42}$ fibrils in step c) as competitor, besides A beta$_{1-42}$ monomer as bait. An elution as separation step is performed for example by pH value reduction as separation step and phage amplification as multiplication.

In this way, 21 peptides which bind specifically to A beta monomer (Mosd 1-21) were developed.

a) "Mosd1" (free N-terminus, amidated C-terminus):
(SEQ ID NO: 1)
YSYLTSYHMVWR b) "Mosd2" (free N-terminus, amidated C-terminus):
(SEQ ID NO: 2)
HTWTTYDYVWRL c) "Mosd3" (free N-terminus, amidated C-terminus):
(SEQ ID NO: 3)
GTMLKFSGMNLT d) "Mosd4" (free N-terminus, amidated C-terminus):
(SEQ ID NO: 4)
HNWFYWTTEPYD e) "Mosd5" (free N-terminus, amidated C-terminus):
(SEQ ID NO: 5)
HNWSWEWWYNPN f) "Mosd6" (free N-terminus, amidated C-terminus):
(SEQ ID NO: 6)
STLHFYTAFLNK g) "Mosd7" (free N-terminus, amidated C-terminus):
(SEQ ID NO: 7)
FSHSHHTWFTWN "Mosd8" (free N-terminus, amidated C-terminus):
(SEQ ID NO: 8)
HFWSWTSLSMTR h) "Mosd9" (free N-terminus, amidated C-terminus):
(SEQ ID NO: 9)
HLSWYWEKYLTS i) "Mosd10 (free N-terminus, amidated C-terminus):
(SEQ ID NO: 10)
HTWTHWFSWNVP j) "Mosd11" (free N-terminus, amidated C-terminus):
(SEQ ID NO: 11)
LSMNITTVHRWH k) "Mosd12" (free N-terminus, amidated C-terminus):
(SEQ ID NO: 12)
VHWDFRQWWQQS m) "Mosd13" (free N-terminus, amidated C-terminus):
(SEQ ID NO: 13)
YSFHFEMNMGNY n) "Mosd14" (free N-terminus, amidated C-terminus):
(SEQ ID NO: 14)
EHWDFGQWWQQS o) "Mosd15" (free N-terminus, amidated C-terminus):
(SEQ ID NO: 15)
GQWDFRQWWQPC -continued p) "Mosd16" (free N-terminus, amidated C-terminus):
(SEQ ID NO: 16)
DWSSRVYRDPQT q) "Mosd17" (free N-terminus, amidated C-terminus):
(SEQ ID NO: 17)
ERSQWGHRDPQS r) "Mosd18" (free N-terminus, amidated C-terminus):
(SEQ ID NO: 18)
DRSKGDHRITQM s) "Mosd19" (free N-terminus, amidated C-terminus):
(SEQ ID NO: 19)
DLRFSSLWKLSH t) "Mosd20" (free N-terminus, amidated C-terminus):
(SEQ ID NO: 20)
VHWDFRQWWQPS u) "Mosd21" (free N-terminus, amidated C-terminus):
(SEQ ID NO: 21)
FSWSMVMPWPTA These peptides according to the invention are claimed as SEQ ID NO: 1 to SEQ ID NO: 21 and can also be used as double peptides or cyclized.

The peptides according to SEQ ID NO: 1-21 can be used as potential medicinal drug against Alzheimer's dementia due to the specific binding to A beta monomers.

A beta monomers are bound highly specifically by peptides according to certain embodiments of the invention, in particular the peptide of SEQ ID NO: 1, whereby oligomers disintegrate.

Within the scope of the invention, it has been found that the existing Aβ monomer-binding substances disadvantageously target the reduction of the Aβ monomers. It has been found that it must be an objective to develop specific binders of the amyloid beta monomer which do not reduce the concentration of the monomer, but instead stabilize the monomers in order to maintain the protective properties thereof.

The peptides according to certain embodiments of the invention address the problem by reducing the amyloid beta oligomer concentration and at the same time stabilizing the amyloid beta monomers. The specificity for A beta monomers can be demonstrated by ELISA.

On the one hand, the aforementioned ligands (or peptides) according to certain embodiments of the invention, which bind specifically to A beta monomers, prevent the formation of A beta oligomers, without also leading to a reduction of the monomer concentration. On the other hand, A beta oligomers already formed are removed from the dynamic equilibrium of the different aggregate species by treatment with a monomer-stabilizing active substance or peptide according to the invention. This advantageously causes the oligomers to be broken down into monomers.

In particular, the formation of oligomers de novo is prevented, and oligomers already formed are removed, more specifically are converted into monomers and also large, non-fibrillar and non-toxic aggregates.

The problem is also addressed by a peptide containing the amino acid sequence according to SEQ ID NO: 1-21 and/or homologues, fragments and parts thereof. This peptide advantageously binds likewise to amyloid beta monomer.

In a variant of the invention, peptides which bind to an A beta monomer of at most 500 µM, preferably 250, 100, or 50 µm, particularly preferably 25, 10 or 6 µM, in particular 4, 2 or 1 µM or sub-µM are used.

The problem is also addressed in particular by polymers which consist of two or more of the above-mentioned peptides according to certain embodiments of the invention and/or homologues or fragments and parts thereof. Dimers are constructed from two of the peptides according to the invention which each bind to amyloid beta species. Here, identical peptides (for example two peptides of SEQ ID NO: 1) or two different peptides according to certain embodiments of the invention can be used (for example a dimer from the peptides according to SEQ ID NO: 1 and SEQ ID NO: 2). Polymers comprise even more peptides according to the invention.

The polymers constructed in accordance with the invention from peptides according to the invention which in turn bind to A beta monomers advantageously demonstrate synergistic effects in respect of their specificity to the A beta monomer. In other words: the polymers according to certain embodiments of the invention are superior to be the individual peptides from which they are constructed. Synergistic effects within the sense of the present invention are effects which demonstrate a higher specificity in relation to the A beta monomer.

In a further particularly advantageous embodiment of the invention, the polymers and in particular dimers in animal model tests (in vitro and in vivo) act advantageously more efficiently than the individual peptide units.

In a variant of the invention, peptides or polymers that bind to an A beta monomer with a disassociation constant ($K_D$ value) of at most 500 µM, preferably 250, 100 or 50 µM, particularly preferably 25, 10 or 1 µM, particularly preferably with a disassociation constant ($K_D$ value) of at most 500 nM, 250, 100 or 50, particularly preferably 25, 10 or 1 nM, 500 µM, 100, 50, 25, 20, 15, 10, 9, 8, 7, 6, 5, 4, 3, 2 or 1 µM to sub-µM are used, wherein any intermediate value can be assumed.

In one embodiment of the invention, the affinity of the binding of the peptides is defined by the disassociation constant ($K_D$ value).

The disassociation constant ($K_D$ value) of a peptide according to the invention is advantageously reduced in an advantageous embodiment of the invention. This is associated with improved properties of the peptides according to certain embodiments of the invention, such as higher affinity of the binding and higher efficacy of the breakdown and/or the prevention of the formation of toxic amyloid beta oligomers. This involves in particular, but not exclusively, a lower $K_D$ value at the high affinity site of the A beta monomer.

Fragments and parts advantageously demonstrate an effect similar or identical to that of the peptides according to the invention.

In certain embodiments of the invention, the peptides according to the invention of SEQ ID NO: 1, SEQ ID NO: 2, SEQ ID NO: 3, SEQ ID 4, SEQ ID NO: 5, SEQ ID NO: 6, SEQ ID NO: 7, SEQ ID NO: 8, SEQ ID NO: 9, SEQ ID NO. 10, SEQ ID NO. 11, SEQ ID NO. 12, SEQ ID NO. 13, SEQ ID NO: 14, SEQ ID NO: 15, SEQ ID NO: 16, SEQ ID NO: 17, SEQ ID NO: 18, SEQ ID NO: 19, SEQ ID NO: 20 and/or SEQ ID NO: 21 and also homologues, fragments and parts thereof consist substantially, preferably to an extent of at least 50%, 60%, 75% or 80%, particularly preferably to an extent of 85%, 90% or 95%, in particular to an extent of 96%, 97%, 98%, 99% or 100%, of D-enantiomeric amino acids.

A polymer within the sense of the invention is formed from 2, 3, 4, 5, 6, 7, 8, 9, 10, 11, 12, 13, 14, 15, 16, 17, 18, 19, 20 or more peptides which bind per se to amyloid beta monomer.

The peptides according to SEQ ID NO: 1-21 are provided with an acid amide group at the free C-terminus in one embodiment of the invention. The peptides according to the invention, for example the peptides according to SEQ ID NO: 1-21 are then amidated at position 12 at the free C-terminus. Dimers hereof are amidated at position 24 at the C-terminus, and so on.

The peptides according to SEQ ID NO: 1-21 are covalently bonded to one another at the free C-terminus with the free N-terminus in a further embodiment of the invention and are then present in cyclized form accordingly. Due to the ring closure, the carboxyl group at the free C-terminus is also advantageously no longer present.

The peptide according to certain embodiments of the invention advantageously has an amino acid sequence in which the cyclization of the linear molecule occurs for example by a covalent bonding of the first amino acid to the last amino acid, for example via a condensation reaction. Of course, further possibilities exist for cyclization, for example by linking other amino acids to one another. The linking of the second amino acid to the last amino acid is mentioned merely by way of example. Any potential other linking is just as conceivable.

In the event that the first and the last amino acid of the peptide are linked to one another, this advantageously results in the fact that there are no open ends present in the peptide chain (amino acid sequence).

This measure also results in the fact that all peptides with linear amino acid sequences which, after the cyclization, give the same, no longer distinguishable amino acid sequence are identical in this sense.

Example: The linear amino acid sequence of the known peptide D3 is rprtrlhthrnr. The corresponding cyclized peptide linked by an amide bond between the N-terminal amino group and the C-terminal carboxyl group "cD3" can no longer be distinguished from the cyclized peptides prtrlhthrnrr, rtrlhthrnrrp, trlhthrnrrpr, rlhthrnrrprt, lhthrnrrprtr, hthrnrrprtrl, thrnrrprtrlh, hrnrrprtrlht, rnrrprtrlhth, nrrprtrlhthr, or rrprtrlhthrn. The cD3 can also still be derived from each of these sequences.

The effects of the higher specificity (and potentially affinity and efficacy) claimed in accordance with certain embodiments of the invention are additionally provided in respect of a binding peptide, preferably even any linear binding peptide, from which a cyclized or otherwise modified peptide according to certain embodiments of the invention can derive.

The preparation of cyclized peptides, for the rest, is prior art and by way of example can be implemented by the method described in DE 102005049537 A1.

The cyclization via the first and last amino acid of the peptide advantageously means that there are no longer any "open" ends of the peptide chain, which are often points of attack for peptide-degrading activities in cells, animals or humans, for example by aminopeptidases and carboxypeptidases.

By means of cyclized peptides according to certain embodiments of the invention, such as Mosd1 according to SEQ ID NO: 1, it is additionally advantageously provided, as side effect, that these cyclized peptides, or polymers according to certain embodiments of the invention in some circumstances are not easily broken down, although this effect is not crucial. As has been presented, this is also true only for the case of a head-to-tail or tail-to-head cyclization, in which both ends of the linear peptide are linked to one another accordingly.

In a further embodiment of the invention, the polymers are constructed from identical peptides, such as Mosd1, or from a combination of 2, 3, 4, 5, 6, 7, 8, 9 or 10 different peptides from the above-mentioned group according to SEQ ID NO: 1-21, as what are known as combination polymers. The peptides can also be identical in part. The number of identical peptides in the combination polymers is freely selectable.

By way of example, polymers can be prepared via chemical synthesis or peptide synthesis.

In one embodiment of the invention, the peptides according to the invention are covalently linked to one another. In a further embodiment, the monomers are not covalently connected to one another.

A covalent connection or linking of the peptide units is present within the sense of the invention if the peptides are linked to one another linearly head-to-head, tail-to-tail or head-to-tail, with or without linkers or linker groups inserted therebetween.

A non-covalent linking in the sense of the invention is present if the peptides are linked to one another by way of example via biotin and streptavidin, in particular streptavidin tetramer.

In a certain embodiment of the present invention, the peptides can be linearly linked to one another, in particular as described above. In another embodiment, the peptides are linked to one another in a branched manner to form the polymer.

A branched polymer, in accordance with certain embodiments of the invention, can be a dendrimer, in which the monomers are linked to one another covalently or non-covalently.

Alternatively, the peptides can also be linked to a platform molecule (such as PEG or sugar) and can thus form a branched polymer.

Alternatively, combinations of these options are also possible.

The peptides according to the invention and polymers herefrom will be referred to hereinafter as peptides according to the invention.

In certain embodiments of the invention, the peptide is one having the amino acid sequence according to SEQ ID NO: 1, SEQ ID NO: 2, SEQ ID NO: 3, SEQ ID 4, SEQ ID NO: 5, SEQ ID NO: 6, SEQ ID NO: 7, SEQ ID NO: 8, SEQ ID NO: 9, SEQ ID NO. 10, SEQ ID NO. 11, SEQ ID NO. 12, SEQ ID NO. 13, SEQ ID NO: 14, SEQ ID NO: 15, SEQ ID NO: 16, SEQ ID NO: 17, SEQ ID NO: 18, SEQ ID NO: 19, SEQ ID NO: 20 and/or SEQ ID NO: 21 and homologues, fragments and parts thereof with an identity of at least 50%.

The term "homologue sequences" or "homologues" within the sense of the invention means that an amino acid sequence has an identity with one of the above-mentioned amino acid sequences of the monomers of at least 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%. Instead of the term "identity", the terms "homologous" or "homology" will be used synonymously in the present description. The identity between two nucleic acid sequences or polypeptide sequences is calculated by comparison with the aid of the BESTFIT program based on the algorithm by Smith, T. F. und Waterman, M. S (Adv. Appl. Math. 2: 482-489 (1981)) with the following parameter settings for amino acids: Gap creation penalty: 8 and Gap extension penalty: 2; and the following parameters for nucleic acids: Gap creation penalty 50 and Gap extension penalty: 3. The identity between two nucleic acid sequences or polypeptide sequences is preferably defined by the identity of the nucleic acid sequence/polypeptide sequence over the entire sequence length in each case, as calculated by comparison with the aid of the GAP program based on the algorithm of Needleman, S. B. and Wunsch, C. D. (J. Mol. Biol. 48: 443-453) with the following parameter settings for amino acids: Gap creation penalty: 8 und Gap extension penalty: 2; and the following parameters for nucleic acids: Gap creation penalty: 50 und Gap extension penalty: 3.

Two amino acids are identical if they have the same amino acid sequence.

In certain embodiments, "homologues" are understood to mean the corresponding retro-inverse sequences of the above-mentioned monomers. The term "retro-inverse sequence" in accordance with certain embodiments of the invention denotes an amino acid sequence which is composed of amino acids in the enantiomeric form (inverse: chirality of the alpha C atom inverted) and in which the sequence order has additionally been reversed compared to the original amino acid sequence (retro=backwards).

In certain further embodiments of the invention, the peptides bind to parts of the amyloid beta peptide.

In certain further embodiments of the invention, the peptides have sequences which differ from the specified sequences by up to three amino acids.

Furthermore, sequences which contain the above-mentioned sequences are also used as peptides.

In certain further embodiments of the invention, the peptides comprise fragments of the above-mentioned sequences or have sequences homologous to the above-mentioned sequences.

The peptide is one for use within the field of medicine, preferably for treating Alzheimer's disease.

In one embodiment of the present invention, the peptide consists substantially of D-amino acids.

The term "substantially of D-enantiomeric amino acids" means that the monomers to be used in accordance with the invention are constructed to an extent of at least 50%, 55%, 60%, 65% or 70%, preferably to an extent of 75% or 80%, particularly preferably to an extent of 85%, 90% or 95%, in particular to an extent of 96%, 97%, 98%, 99% or 100%, from D-enantiomeric amino acids.

In certain further embodiments of the invention, a peptide is a peptide for inhibiting fibril formation of amyloid beta oligomers. The peptides according to certain further embodiments of the invention detoxify the A beta oligomers or polymers formed therefrom, and also fibrils, by not binding thereto, but instead binding to A beta monomer, and lead by the equilibrium to the reduction of the A beta oligomers and thus convert these into non-toxic compounds. Accordingly, a further embodiment of the present invention is a method for detoxifying the A beta oligomers, and aggregates or fibrils formed therefrom.

In one embodiment, a further subject of the invention is constituted by peptides according to the invention which are linked to a further substance.

The linking is a chemical binding as defined in Rompp's Chemistry Lexicon, 9$^{th}$ edition, volume 1, page 650 ff., Georg Thieme publishers Stuttgart, preferably a primary valency bonding, in particular a covalent bonding.

The substances, in a variant, are pharmaceuticals or active substances, defined in accordance with the German Pharmaceutical Products Act § 2 and § 4 (19), as at September 2012. In an alternative, active substances are therapeutically active substances which are used as pharmaceutically active substances. Anti-inflammatories are preferably used.

In certain further embodiments of the invention, the substances are compounds which intensify the effect of the peptides.

In an alternative, such compounds are aminopyrazole and/or aminopyrazole derivatives. Aminopyrazole derivatives in the sense of the invention are 3-aminopyrazole-5-carboxylic acid or 3-nitropyrazole-5-carboxylic acid and all derivatives thereof in which the heterocyclic CH group has been swapped for —CR— or —N— or —O— or —S—, and all peptide dimers, trimers or tetramers derived therefrom, preferably aminopyrazole trimer.

In certain further embodiments of the invention, the compounds are compounds which improve the solubility of the peptides and/or the passage through the blood-brain barrier.

In certain other embodiments of the invention, the peptides have any arbitrary combination of at least two or more features of the above-described variants, embodiments and/or alternatives.

It has also been found that amidated and/or cyclized peptides, compared to linear binding peptides in which the free C-terminus, i.e. the C-terminal carboxyl group, is not modified and accordingly carries a negative charge, bind with a higher affinity to A beta monomer. This means that the $K_D$ value of the modified peptides is lower than that of linear peptides in which the free C-terminus, i.e. the C-terminal carboxyl group, is not modified and accordingly carries a negative charge.

In a further preferred embodiment of the invention, the affinity of the bonding of the peptides modified in accordance with the invention without negative charge at the C-terminus is therefore increased, compared to linear peptides with negative charge at the C-terminus, but apart from that identical amino acid sequence, by 1%, 2, 3, 4, 5, 6, 7, 8 or 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99, in particular 100%, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198 or 199, in particular 200%, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298 or 299, in particular 300%, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398 or 399, in particular 400%, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 or 499, advantageously even 500%, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598 or 599, particularly advantageously 600%, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698 or 699, particularly advantageously 700%, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798 or 799, also particularly advantageously 800%, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898 or 899, also particularly advantageously 900%, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998 or 999, or even by 1,000%, or even by 10,000% or even by up to 100,000% or 1,000,000%, wherein any intermediate value can be assumed. This concerns in particular the increased affinity to the high affinity site of the A beta monomer.

This is demonstrated by an accordingly reduced $K_D$ value. The $K_D$ value as a measure for the affinity of the bonding of a modified, in particular cyclized peptide to amyloid beta monomer is reduced, compared to a linear binding peptide with negative charge at the free C-terminus, by 1%, 2, 3, 4, 5, 6, 7, 8 or 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99, in particular 99.1, 99.2, 99.3, 99.4, 99.5%, 99.6, 99.7, 99.8, or 99.9 up to 99.99 or even 99.999%, wherein any intermediate value can be assumed.

These lower $K_D$ values relate advantageously in particular, but not exclusively, to the high affinity site of A beta species monomer.

The modified peptides can therefore be used even more efficiently as probes for diagnostic purposes, as linear, binding peptides with negative charge at the free C-terminus, in particular are also used more efficiently than their linear peptide pendants with identical amino acid sequence.

They can be also be used, however, in particular more efficiently than therapeutic agents, as linear, binding peptides with negative charge at the free C-terminus, in particular more efficiently than their linear peptide pendants with identical amino acid sequence.

In a direct comparison of a modified peptide and a peptide with negative charge at the C-terminus, the peptide according to the invention performs better in respect of affinity and efficacy.

It has also been found that the modified peptides, compared to peptides with negative charge at the free C-terminus, but in particular compared to their peptide pendants with identical amino acid sequence, additionally prevent the formation of particularly toxic amyloid beta oligomers or cause the destruction and/or detoxification thereof, also with a higher efficacy or efficiency. This efficacy is in particular increased by 1%, 2, 3, 4, 5, 6, 7, 8 or 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9, particularly advantageously even by 100%.

In the simplest case, a sample with the different A beta conformers is fractionated for testing, for example. Different conformers, such as monomers, oligomers, fibrils or higher aggregates are enriched in each fraction in accordance with the fractionation step and can then be exactly determined.

The term "exactly determined" comprises a calibration step in the fractionation by molecules of known type and behavior. After the fractionation, only a specific type of conformers of the A beta is present in each fraction, for example monomers, oligomers or fibrils, and so on.

By way of example, the conformers are separated in accordance with their s-value or sedimentation coefficient in a density gradient centrifugation as fractionation step. Molecules of different size can have an identical hydrodynamic radius, yet can still have different s-values and are also separated on this basis. Due to a calibration with molecules of known s-value, the A beta conformers obtained by means of density gradient centrifugation are exactly determined on the basis of their s-value.

The obtained fractions are then treated with and without active substance and are identified for example by RP-HPLC. The efficacy of the active substance can be determined in this way.

Certain further embodiments of the invention including a method will be presented hereinafter. What is known as the QIAD test (quantitative determination of interference with Aβ aggregate size distribution) can be used for the quantitative analysis of active substances. The method for quantitative analysis of the influence of an active substance on the particle size distribution of amyloid peptides and/or proteins in a sample has the following steps: A beta is first left to aggregate under controlled conditions, so that different A beta aggregates form. The conditions are selected so that a particularly large amount of small, particularly cytotoxic A beta oligomers are formed. The substance to be examined, for example one of the modified peptides according to certain embodiments of the invention, is then added to the sample. The active substance changes the particle size distribution in the sample. This change is determined quantitatively. The change is a measure for the reduction or even for the complete elimination of specific toxic species of a specific particle size. Due to the QIAD method, the increase or decrease of A beta aggregates of a specific particle size is measured. Whereas some A beta aggregates with a specific size were initially present in the sample, these are reduced or even completely eliminated under the influence of the active substance. Other particle sizes increase or remain constant under the influence of the active substance. The particles formed from the A beta are preferably separated from one another on the basis of their hydrodynamic radius. In this way, multiple fractions are advantageously obtained from the sample. The particles in the fractions are enriched with amyloid peptides and/or proteins having a specific aggregate size. This separation of the particles can be implemented by means of density gradient centrifugation. The fractions are physically separated from one another, for example by being pipetted off. The concentration of A beta in the respective fractions is then determined by a complete denaturing of the A beta species during a reversed-phase (RP-)HPLC performed subsequently to the fractionation. The denaturing of the aggregates can occur completely for example with 30% acetonitrile and 0.1% trifluoroacetic acid at a column temperature of 80° C., and the aggregates can be separated on a C8 column on the basis of hydrophobicity. Eluting A beta is detected by means of UV absorption at 215 nm. The peak area integration can be performed by means of Agilent Chemstation software. The offsetting of resultant values against a previously performed calibration allows the calculation of the concentration of the A beta present in the respective fractions. The mean value from a number of experiments carried out independently of one another (for example six) with the resultant standard deviation can be calculated for each fraction. The advantage of HPLC analysis lies in the fact that a very sensitive detection (for example approximately 20 nM or 1.8 ng Aβ1-42) and reliable quantification can be provided regardless of the state of aggregation and a solvent. An advantage of the method lies in the coupling of density grade centrifugation and reversed-phase HPLC, which also makes possible a reliable quantification of A beta oligomers.

The effect according to certain embodiments of the invention of an increased efficacy of the elimination (or formation) of amyloid beta species and in particular amyloid beta oligomers can be achieved with one of these methods, but not exclusively with these methods.

In a particularly preferred embodiment of the invention, the effects of the increased specificity in respect of A beta monomer and the associated simultaneous efficacy of the elimination or detoxification of A beta oligomers (or the formation thereof) also occur in vitro and/or in vivo.

Certain embodiments of the invention also relate to a composition containing the peptide, in particular for treating Alzheimer's disease.

Certain further embodiments of the invention relate to a composition containing the peptide according to the invention, in particular for the reduction of any toxic A beta oligomers present and for the prevention of the formation of toxic A beta oligomers.

The "composition" according to certain embodiments of the invention can be, for example, a vaccine, a medicinal drug (for example in tablet form), an injection solution, or a foodstuff or food supplement containing the peptide according to the invention in a formulation that is to be prepared on the basis of expert knowledge.

The invention also relates to a kit containing a ligand or peptide according to the invention.

In a kit of this type, the peptides according to certain embodiments of the invention can be packaged in containers, optionally with/in buffers or solutions. All components of the kit can be packaged in the same container or separately from one another. The kit can also contain instructions for use thereof. A kit of this type by way of example can contain the peptides according to the invention in an injection vial with stopper and/or septum. Furthermore, a disposable syringe can also be contained, by way of example.

The peptides according to certain embodiments of the invention can serve as probes for binding to A beta monomer. Such molecular probes contain the peptide or polymer according to the invention and optionally dyes, fluorescence dyes, radioactive isotopes (PET, etc.), gadolinium (MRI) and alternative substances suitable for the imaging of the probes and can be injected for example intravenously into the patient. Once they have passed over the blood-brain barrier, the probes can bind to A beta monomers and/or plaques. The A beta monomers and/or plaques thus labeled can be made visible by means of imaging methods, such as SPECT, PET, CT, MRT, proton MR spectroscopy, etc.

Furthermore, the invention also relates to the use of the peptide according to the invention for the prevention of amyloid beta oligomers and/or amyloid beta peptide aggregates and/or amyloid beta fibrils.

The peptide according to certain embodiments of the invention is also used for the detoxification of toxic amyloid beta oligomers and/or aggregates. In particular, it is used in order to bind to amyloid beta monomers and to form amorphous, non-toxic aggregates by shifting the equilibrium.

Figure 2:
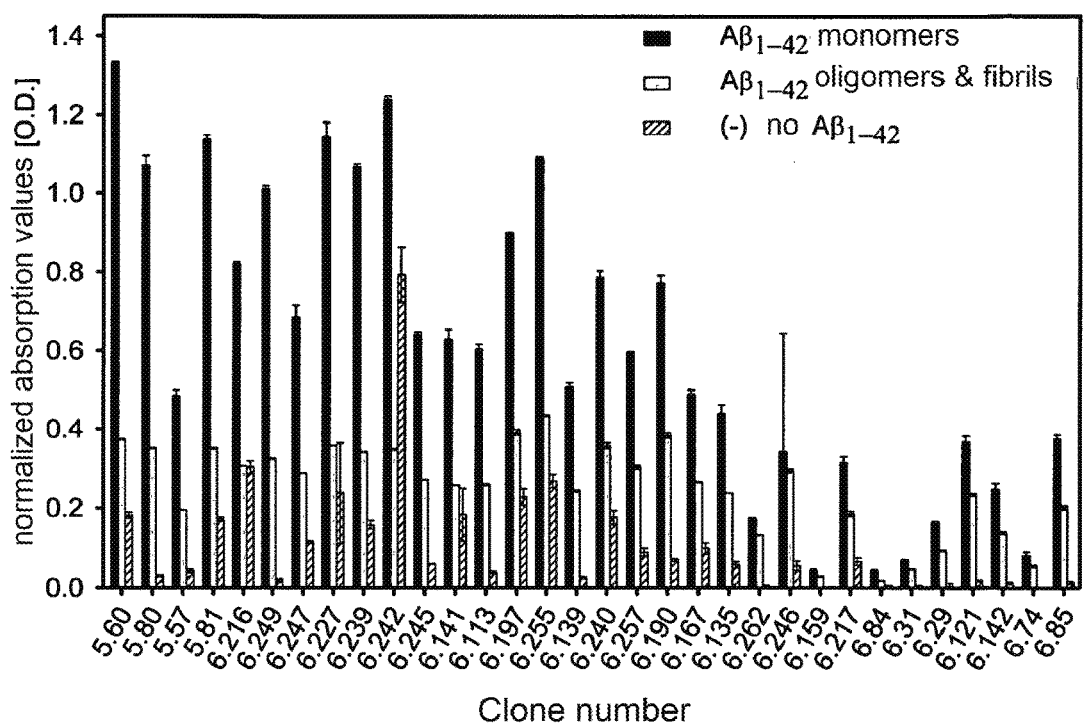
FIG. 2: shows a monoclonal phage ELISA.

These aggregates can consist of bound monomers, and the equilibrium is shifted, primarily away from the oligomers. Amorphous, non-toxic aggregates can be formed, whereby a reduction of the toxic species is achieved. Other peptides stabilize the A beta monomers by the monomer specificity in the ELISA test, as shown in FIG. 2.

It has been found that if A beta oligomers are already present, the objective of treatment must be to address these by substances that have the highest possible specificity to A beta monomer. In fact, the specificity with respect to A beta monomer compared to A beta oligomer can never be high enough, and the corresponding ratio is in any case greater than 1.

It has been found that A beta monomers, as building blocks of A beta oligomers, are produced constantly in the human body and do not appear to be toxic per se. It is even possible that monomers might have a positive function. A beta monomers can randomly amalgamate depending on their concentration. The concentration is dependent on their rate of formation and rate of breakdown in the body. If an increase of the concentration of A beta monomers in the body takes place with increasing age, a spontaneous amalgamation of the monomers to form A beta oligomers becomes increasingly likely. The resultant A beta oligomers could multiply similarly to prions and ultimately could lead to Alzheimer's disease.

It has also been found that an important difference between prevention and treatment or even curing of Alzheimer's dementia lies in the fact that prevention might be achieved already by the prevention of the formation of the first A beta oligomers. Just a few highly specific A beta monomer ligands which at the same time have low affinity and selectivity in respect of A beta oligomers are sufficient for this purpose.

The formation of the A beta oligomers from many monomers is a high order reaction and is therefore highly dependent on the A beta monomer concentration. Even a small reduction of the active A beta monomer concentration thus leads to a prevention of the formation of the first A beta oligomers. The more preventative treatment concepts and substances previously in development are presumably based on this mechanism.

However, in the case of the treatment of Alzheimer's dementia, a completely altered situation is concerned. Here, A beta oligomers or possibly also already larger polymers or fibrils are present, which multiply by prion-like mechanisms. This multiplication, however, is a low order reaction and is hardly at all dependent on the A beta monomer concentration.

If A beta oligomers are thus already formed, the objective of a treatment must be to address these by substances which eliminate them particularly efficiently and/or particularly efficiently prevent their formation or detoxify them.

These requirements in respect of the treatment of Alzheimer's dementia are met with the provision of the peptides according to certain embodiments of the invention. The peptides according to certain embodiments of the invention, within the scope of the treatment, bind the amyloid beta monomers specifically with an accordingly low disassociation constant. A further subject is thus the use of the peptides according to certain embodiments of the invention as a therapeutic agent for the treatment of Alzheimer's disease.

The peptides according to certain embodiments of the invention bind particularly well to A beta at soluble A beta monomers.

It can be demonstrated by means of the Thioflavin T test that the peptides according to certain embodiments of the invention very efficiently inhibit fibril formation of A beta peptides, particularly the peptide with the SEQ ID NO: 1-21, in particular the peptide according to SEQ ID NO: 1.

Certain further embodiments of the invention relate to the use of the peptides in a method for the treatment (in vitro, ex vivo) of blood, blood products and/or organs, characterized in that the blood, the blood products and/or organs taken from the human or animal body and A (amyloid) beta oligomers are removed and/or detoxified.

The specificity of the peptide results from the difference in % of the absorption values for the target molecule or the bait (for example A beta monomer) and the normalized absorption values for the competitors (for example A beta oligomers and fibrils) in the monoclonal phage ELISA.

The absorption values then constitute the affinity of individual phage clones for a particular immobilized A beta species. Here, the specificity is not dependent on the strength of the affinity, but instead only on the difference of the affinities between the species. The greater is the difference in % of the signal strength for the target molecule (for example $A\beta_{1-42}$ monomer) from the signal strength for what are known as the competitors ($A\beta_{1-42}$ oligomers and fibrils), the more specifically the phage in question binds to the target molecule. The terms "competitors" and "target molecule" or "bait" are defined as specified below.

In the sense of the above-mentioned concept of specificity, peptides are considered to be specific if the difference in % between the normalized absorption values (with target molecule, for example monomeric $A\beta_{1-42}$=100%) is at least 40%, 45%, even better 50%, preferably better than 70%, in particular better than 80% or 90%, and particularly preferably 100%, wherein all intermediate values can be assumed.

Changing substrates initially increase the general specificity for the target molecule, but also "relatives" thereof. The specificity for the target molecule with respect to non-specifically binding phages (binding to substrate (plastics surfaces), streptavidin or BSA (blocker reagent)) is increased with the aid of changing substrates and the alternating blocking and non-blocking thereof.

Due to the alternating use of different substrates, phages which have bonded to substrate A for example in round X can no longer bind their preferred binding partner substrate A in the following round X+1 because this has been replaced by substrate B, and therefore phages binding substrate A are lost.

In addition to this first, rough specification, an increase of the specificity for a clearly defined form of the target molecule (for example monomers) was achieved with the aid of the use of the competitors, which for example can represent polymers of the target molecule.

In this way, not only could the previously frequently occurring non-specific binding to target molecule and substrate or the preferred binding to substrate be significantly reduced, but the specificity to a clearly defined structural, monomeric variant of the target molecule could be increased.

The method according to certain embodiments of the invention is therefore advantageously particularly suitable for the identification of ligands in respect of A beta monomer or A beta oligomer as bait with the other species as competitor.

Example: It is practically impossible to ensure the same immobilization efficiency for example for different $A\beta_{1-42}$ species for ELISA experiments, and therefore an immobilization control should be used on each 96-well microtiter plate. This can lie in the fact that, instead of the amplified individual phage clone a ($A\beta_{1-42}$-)specific antibody (for example 6E10) can be added to the respective control reaction trays (wells). The measured absorption signal, the strength of which is dependent on the binding of an antibody to the offered surface with or without immobilized $A\beta_{1-42}$ species, can be used following the experiment as a measure for the immobilization efficiency. A possible cross-reaction of the phage-specific antibody with the immobilized molecules or the surface of the reaction tray can be examined as further control. The phage-specific antibody is normally added to the batches in which individual phages are tested in order to quantify the binding thereof to the given target structure (for example surface, $A\beta_{1-42}$ monomers, $A\beta_{1-42}$ oligomers and fibrils). For this purpose, it must be known, however, how strong the phage-specific antibody binds non-specifically to other possible targets, for example to the above-mentioned potential target structures of the phages themselves in order to include these 'cross-reactions' as appropriate in the interpretation of the data obtained.

A method for normalizing the obtained values should therefore be performed. From all absorption values of the individual phage clone in the monoclonal phage ELISA, the values of the phage antibodies tested for cross-reaction can be used as background. This occurs in accordance with the previously immobilized species. The signal values of the phage antibody from the reaction trays with immobilized $A\beta_{1-42}$ oligomers for this purpose can be removed from the signal values of the individual phage clone from the reaction trays with immobilized $A\beta_{1-42}$ oligomers. A similar process is then carried out for $A\beta_{1-42}$ monomers. In this way, a possible background signal of the phage antibody can initially be calculated from the signals of the individual phage clone. On the basis of the control with $A\beta_{1-42}$-specific 6E10 antibodies, the immobilization efficiency of the different used $A\beta_{1-42}$ species is then measured and compared. A more effective immobilization of the mixture of $A\beta_{1-42}$ oligomers and fibrils compared to the $A\beta_{1-42}$ monomers is thus advantageously achieved (see also FIG. 1). More potential binding partners for the individual phage clone are therefore offered in the reaction trays in which $A\beta_{1-42}$ oligomers and fibrils are immobilized, and this distorts the result. The values of the 6E10 control from the reaction trays in which $A\beta_{1-42}$ oligomers and fibrils were immobilized have therefore been normalized to the content of $A\beta_{1-42}$ in the reaction trays in which $A\beta_{1-42}$ monomers were immobilized. This results, for each used microtiter plate, in a specific factor by which the values for the binding to $A\beta_{1-42}$ oligomers and fibrils of each individual phage clone have been multiplied. Only in this way is an equal interpretation of the results particularly in respect of the assessment of the specificity of the individual phage clone possible (see FIG. 2).

EXAMPLES

The invention will be explained hereinafter in greater detail on the basis of practical examples and the accompanying drawings, without hereby being limited.

Competitive Mirror-Image Phage Display on the Basis of the Example of a Beta Monomer as Bait:

The objective of the competitive mirror-image phage display was the selection of peptides specifically binding $A\beta_{1-42}$ monomer. Six 'panning rounds' were performed, wherein one panning round corresponded to the process in which the phage library is brought into contact with the immobilized target molecule/bait ($A\beta_{1-42}$ monomers).

In order to reduce the number of phages which have an increased specificity to other $A\beta_{1-42}$ species, that is to say comprise oligomers and fibrils, these species were used as competitors from the second panning round.

In this way, the number of phages having an increased affinity to $A\beta_{1-42}$ oligomers and fibrils could be reduced, and the number of phages having an increased specificity for $A\beta_{1-42}$ monomers could be enriched at the same time.

With the further objective of reducing the enrichment of plastics-binding phages and phages having a specificity for the blocking reagent BSA (bovine serum albumin), the target molecule was immobilized on different streptavidin-coated plastics/surfaces (polystyrene/polypropylene/polycarbonate), alternating from round to round.

The polystyrene surfaces were washed in accordance with the manufacturers instructions prior to the immobilization of the target molecule. In addition, a blocking and non-blocking of the surface with 150 µl 1×TBS/0.1% (v/v) Tween-20/1% (w/v) BSA was performed in alternation from one round to the next prior to the immobilization of the target molecule for one hour at room temperature. In this way, no combination of plastics surface and blocking was used more than once during the 6 panning rounds (see Table X).

This step was carried out in order to reduce non-specific binding to the plastics and BSA, since for example phages which had bonded to BSA could not find a binding partner in the following panning round, which was carried out without BSA in accordance with the above explanation, and were removed accordingly in the washing steps.

Following the pre-treatment of the surface, D-enantiomer, N-terminal biotinylated $A\beta_{1-42}$ monomers were diluted in 1×TBS to a concentration of 63 nM and were immobilized as target molecule on the surface in question. The monomer status of the $A\beta_{1-42}$ molecules was guaranteed via size exclusion chromatography. The used concentration of 63 nM corresponds to the occupancy of ⅓ of all streptavidin binding points per used surface, starting from the surface with the smallest number of free streptavidin binding points. 100 µl of the solution of monomeric $A\beta_{1-42}$ in 1×TBS set to 63 nM were placed on the streptavidin-coated surface and incubated for 5 minutes at room temperature. The surface was then washed three times with 150 µl 1×TBS.

In the first panning round, 90 µl 1×TBS were then placed with 10 µl of the commercially obtainable recombinant phage library on the surface and incubated for 5 minutes at room temperature. The supernatant was removed and replaced with 100 µl 10 µM biotin in 1×TBS/0.1% (v/v) Tween-20. This step, by means of the highly affine streptavidin binding partner biotin, served for the competitive displacement of phages which had bonded to streptavidin binding points that were still free and was carried out for 5 minutes at room temperature. The surface was then washed four times with 1×TBS/0.1% (v/v) Tween-20.

The phages still bound were removed by a pH step. For this purpose, 100 µl of a 0.2 M glycine/HCl solution with a pH value of 2.2 were placed on the surface and incubated for 10 minutes at room temperature. The solution inclusive of the eluted phages was removed and added to and mixed with 25 µl 1 M Tris/HCl with a pH value of 9.1 for neutralization.

20 µl of this batch were transferred into a new reaction vessel and served to determine the phage titer after elution ('output titer').

The remaining 105 µl were used for amplification of the eluted phages. Both titration and amplification were performed in accordance with instructions of the manufacturer of the phage library (prior art).

The amplified phages were titrated similarly to the eluted, non-amplified phages (input titration). The number of plaque-forming units (pfu) per millimeter was determined under consideration of the dilution factor. The phage number was set on the basis of this number for each round to $1 \times 10^{11}$ phages in 100 µl 1×TBS. For each subsequent round, the amplified phages of the previous round were used and diluted accordingly.

Whereas the concentration of the target molecule or bait (monomeric $A\beta_{1-42}$) remained stable in all rounds at 63 nM, the competitors were added in increasing concentration from one panning round to the next. D-enantiomer, $A\beta_{1-42}$ oligomers (purified, that is to say separated from other $A\beta_{1-42}$ species by means of size exclusion chromatography) and $A\beta_{1-42}$ fibrils (purified by means of density gradient centrifugation) were used as competitors. These competitors were not biotinylated, since otherwise binding to the surface would have been possible. The objective, however, was to separate competitor-binding phages from the phages which had bonded to the immobilized target molecule by washing them off during the washing steps. The increase in the concentrations was the same for both competitor species and was as follows: round 1=0 nM, round 2=1 nM, round 3=5 nM, round 4=10 nM, round 5=50 nM, round 6=500 nM.

By introducing the competition step, the above-described sequence of a panning round was adapted from round 2 as follows: $1 \times 10^{11}$ phages from the previous round henceforth were not diluted in 100 µl 1×TBS, but in 60 µl. The remaining 40 µl were filled up directly thereafter with 20 µl 1×TBS inclusive of a fivefold increase in the concentration of $A\beta_{1-42}$ oligomers specified above for each round and 20 µl 1×TBS inclusive of a fivefold increase in the above-specified concentration of $A\beta_{1-42}$ fibrils. The increase by a factor of five of the above-specified concentrations results from the fact that the concentration was calculated on the basis of the total volume of 100 µl; since in each case only a fifth of the total volume (20 µl) consisted of competitor solutions, the concentration of the competitors in the total batch corresponded to the specified values.

After 5 minutes the solution of phages and competitors was removed. The competition step already described with 10 µM biotin and the washing steps then followed, the number of these also being increased from one panning round to the next (round 1=4 washing steps, round 2=6, round 3=8, round 4=10, round 5=12, round 6=15).

TABLE 1

Parameters of all 6 panning rounds performed.

| Round | Plastics | Pre-washes | Blocking with BSA | Target molecule concentration | Competitor concentration | Number of washing steps |
|---|---|---|---|---|---|---|
| 1 | PS | Yes | Yes | 63 nM | 0 nM | 4 |
| 2 | PP | No | No | 63 nM | 1 nM | 6 |
| 3 | PC | No | Yes | 63 nM | 5 nM | 8 |
| 4 | PS | Yes | No | 63 nM | 10 nM | 10 |
| 5 | PP | No | Yes | 63 nM | 50 nM | 12 |
| 6 | PC | No | No | 63 nM | 500 nM | 15 |

Table 1: The following parameters were determined for the mirror-image phage display. Within 6 panning rounds, 3 different plastics were used in alternation as surface (PS=polystyrene, PP=polypropylene, PC=polycarbonate). In addition, in each second round starting with the first, the surface was blocked with BSA before the target molecule was immobilized. In this way, an enrichment of phages with a specificity for one of the plastics or BSA should be reduced. Since the nave phage library (here, nave means that it had not been brought previously into contact with the target molecule) had the possibility to bind in the first panning round to the immobilized target molecule ($A\beta_{1-42}$ monomer), a competition step was introduced from the second panning round. This step consisted of the addition of rising concentrations of competitors, specifically $A\beta_{1-42}$ oligomers and fibrils. In this way, phages which bind non-specifically to different $A\beta_{1-42}$ species should be removed, so that ultimately only the phages remain that a) bind specifically to D-enantiomeric $A\beta_{1-42}$ and not to plastics surfaces, BSA or biotin, and b) are specific for monomeric, D-enantiomeric $A\beta_{1-42}$. The rigorousness during the washing was increased by increasing the number of washing steps per round, so that phages binding very weakly to the target molecule should have been removed.

Monoclonal Phage Amplification:

Accumulations of different phages binding increasingly more specifically to the target molecule were provided from the panning rounds. From these accumulations, individual phage clones were multiplied in order to then compare these with one another (DNA sequencing and monoclonal phage ELISA). For this purpose, plaque-forming units present individually were removed from the output titer plates of the preferred rounds of the mirror-image phage display (panning rounds 3-6) and were multiplied. The multiplication was performed in accordance with a protocol specified by the manufacturer of the recombinant phage library.

Monoclonal Phage ELISA:

The affinity of individual phage clones with respect to the target molecule and the competitors was examined by means of ELISA. For this purpose, all three species were immobilized in biotinylated form on a polystyrene surface at streptavidin bound thereon. Since, during the panning rounds, oligomers and fibrils were added at the same time as competitors, these two species were immobilized in the monoclonal phage ELISA, likewise mixed. The $A\beta_{1-42}$ species were purified in accordance with the same principle as in the mirror-image phage display and were immobilized at 320 nM (in the case of $A\beta_{1-42}$ oligomers and $A\beta_{1-42}$ fibrils, a 1:1 mixture of both species with a total concentration of 320 nM was produced and immobilized). For each clone and each control mentioned during the subsequent course of the protocol, $A\beta_{1-42}$ monomers, $A\beta_{1-42}$ oligomers/fibrils or neither of the two batches were immobilized in each case in 2 reaction trays (technical term, also referred to in principle as "wells": 96 on a polyester (or other plastics) plate). The reaction trays without immobilized $A\beta_{1-42}$ served later for detection as to whether the phages or the antibodies used for detection of the phages or of the $A\beta_{1-42}$ had bonded non-specifically to the plastics surface. The streptavidin-coated microtiter plates were pre-washed as specified by the manufacturer. The $A\beta_{1-42}$ monomers or the $A\beta_{1-42}$ oligomers and fibrils were diluted in each case to a concentration of 320 nM in 1×TBS. For immobilization, 100 µl were used per reaction tray and were incubated for 15 minutes at room temperature. After having washed the entire plate(s) twice with 150 µl 1×TBS per reaction tray, a blocking step with 150 µl 1×TBS/0.1% (v/v) Tween-20/1% (w/v) BSA was performed for an hour at room temperature. Three washing steps with 150 µl 1×TBS/0.1% (v/v) Tween-20 then followed per reaction tray. The amplified individual phage clones were mixed 1:1 with 1× TBS/1% (w/v) BSA. The antibody 6E10 was diluted 1:10,000 in 1×TBS/0.1% (v/v) Tween-20. 100 µl of each individual phage clone dilution, a sample without phages (LB medium 1:1 with 1×TBS/1% (w/v) BSA) and the antibody dilution were placed, in each case, on 2 reaction trays without immobilized $A\beta_{1-42}$, 2 reaction trays with immobilized monomeric $A\beta_{1-42}$, and 2 reaction trays with immobilized oligomeric/fibrillar $A\beta_{1-42}$ and incubated for one hour at room temperature. After washing five times with 150 µl 1×TBS/0.1% (v/v) Tween-20 per reaction tray, 200 µl 1×TBS/0.1% (v/v) Tween-20 were placed in each reaction tray, and the plate(s) incubated for one hour at room temperature. The solutions were removed and replaced as follows: In all reaction trays that had been incubated previously with individual phage clone dilutions or the batch without phages, 100 µl of a phage antibody diluted 1:5,000 in 1×TBS/0.1% (v/v) Tween-20 were now added. The enzyme horseradish peroxidase (HRP) was coupled to this antibody and later served for the conversion of a substrate (TMB). This conversion resulted in a color reaction of which the strength is proportional to the binding of the antibody to its target (phage) and thus in turn is proportional to the binding of the phages to the immobilized species or the surface. At the same time, 100 µl of a second antibody diluted 1:1,000 in 1×TBS/0.1% (v/v) Tween-20 were now added to all reaction trays that had been previously incubated with the dilution of the 6E10 antibody, said second antibody being able to identify and bind to the 6E10 antibody originating from mice. This antibody is also HRP-coupled and thus allows a quantification of the binding of the first antibody to the immobilized target molecules or the plastics surface of the reaction tray. After one hour of incubation at room temperature, the plate(s) was/were washed 10 times with 150 μl 1×TBS/0.1% (v/v) Tween-20 per reaction tray. The signal was detected by adding the substrate 3,3',5,5'-tetramethylbenzidine (TMB). TMB is converted from HRP, wherein this results in a color change in the solution. The strength of the color reaction is a measure the binding strength of the phages or of the antibody. 50 μl of the TMB solution are applied for this purpose per reaction tray after the washing. The development of color is stopped by adding 50 μl 2 M $H_2SO_4$ as soon as the solutions in the reaction trays have become turquoise. The absorption at 450 nm is then read automatically.

The values obtained in the monoclonal phage ELISA for the affinity to $A\beta_{1-42}$ oligomers and fibrils were firstly normalized, on the basis of the results of the immobilization control with $A\beta_{1-42}$-specific antibody 6E10 (see FIG. 1, immobilization control), to the $A\beta_{1-42}$ content of the $A\beta_{1-42}$ monomer-coated reaction trays. The values of the signal strength for monomer-coated reaction trays were then set to 100% for each clone. The difference in the signal strength for $A\beta_{1-42}$ oligomer- and fibril-coated reaction trays from the values for $A\beta_{1-42}$ monomer-coated reaction trays is given in % in Table 2 below. The higher is the value, the greater is the difference and the more specific is the binding to $A\beta_{1-42}$ monomers. Different clones were identified by the method according to the invention (clones 5.60-6.135), followed by further tested, but not selected clones (6.262-6.85). Clone 6.84 for example was not selected for further experiments, because although the specificity to $A\beta_{1-42}$ monomers was provided, the signal strength was extremely low.

TABLE 2

$A\beta_{1-42}$ monomer specificity of the individual phage clones in accordance with monoclonal phage ELISA.

| Clone number | Name | Difference in signal strength between Aβ1-42 monomers (100%) and Aβ1-42 oligomers and fibrils |
|---|---|---|
| >5.60 | Mosd1 | 71.989 |
| >5.80 | Mosd2 | 67.145 |

TABLE 2-continued $A\beta_{1-42}$ monomer specificity of the individual phage clones in accordance with monoclonal phage ELISA.

| Clone number | Name | Difference in signal strength between Aβ1-42 monomers (100%) and Aβ1-42 oligomers and fibrils |
|---|---|---|
| >5.57 | Mosd3 | 59.955 |
| >5.81 | Mosd4 | 69.154 |
| >6.216 | Mosd5 | 62.729 |
| >6.249 | Mosd6 | 67.981 |
| >6.247 | Mosd7 | 57.960 |
| >6.227 | Mosd8 | 68.616 |
| >6.239 | Mosd9 | 68.016 |
| >6.242 | Mosd10 | 71.902 |
| >6.245 | Mosd11 | 57.671 |
| >6.141 | Mosd12 | 59.012 |
| >6.113 | Mosd13 | 57.246 |
| >6.197 | Mosd14 | 56.526 |
| >6.255 | Mosd15 | 59.985 |
| >6.139 | Mosd16 | 52.387 |
| >6.240 | Mosd17 | 54.492 |
| >6.257 | Mosd18 | 49.181 |
| >6.190 | Mosd19 | 50.299 |
| >6.167 | Mosd20 | 45.718 |
| >6.135 | Mosd21 | 46.030 |
| >6.262 | | 23.317 |
| >6.246 | | 14.335 |
| >6.159 | | 31.283 |
| >6.217 | | 40.973 |
| >6.84 | | 55.362 |
| >6.31 | | 33.755 |
| >6.29 | | 42.783 |
| >6.121 | | 36.403 |
| >6.142 | | 43.606 |
| >6.74 | | 33.181 |
| >6.85 | | 46.352 |

With the mirror-image phage display according to the invention, Mosd1 to Mosd21 were determined to be peptides specifically binding to A beta monomer.

TABLE 1

Selected peptide sequences specifically binding $A\beta_{1-42}$ monomer which were selected by means of competitive mirror-image phage display in accordance with the invention.

| Clone number | Name | SEQ ID NO: | Amino acid sequence |
|---|---|---|---|
| >5.60 | Mosd1 | 1 | YSYLTSYHMVWR |
| >5.80 | Mosd2 | 2 | HTWTTYDYVWRL |
| >5.57 | Mosd3 | 3 | GTMLKFSGMNLT |
| >5.81 | Mosd4 | 4 | HNWFYWTTEPYD |
| >6.216 | Mosd5 | 5 | HNWSWEWWYNPN |
| >6.249 | Mosd6 | 6 | STLHFYTAFLNK |
| >6.247 | Mosd7 | 7 | FSHSHHTWFTWN |
| >6.227 | Mosd8 | 8 | HFWSWTSLSMTR |
| >6.239 | Mosd9 | 9 | HLSWYWEKYLTS |
| >6.242 | Mosd10 | 10 | HTWTHWFSWNVP |
| >6.245 | Mosd11 | 11 | LSMNITTVHRWH |

TABLE 1-continued

Selected peptide sequences specifically binding Aβ$_{1-42}$ monomer which were selected by means of competitive mirror-image phage display in accordance with the invention.

| Clone number | Name   | SEQ ID NO: | Amino acid sequence |
|--------------|--------|------------|---------------------|
| >6.141       | Mosd12 | 12         | VHWDFRQWWQQS        |
| >6.113       | Mosd13 | 13         | YSFHFEMNMGNY        |
| >6.197       | Mosd14 | 14         | EHWDFGQWWQQS        |
| >6.255       | Mosd15 | 15         | GQWDFRQWWQPC        |
| >6.139       | Mosd16 | 16         | DWSSRVYRDPQT        |
| >6.240       | Mosd17 | 17         | ERSQWGHRDPQS        |
| >6.257       | Mosd18 | 18         | DRSKGDHRITQM        |
| >6.190       | Mosd19 | 19         | DLRFSSLWKLSH        |
| >6.167       | Mosd20 | 20         | VHWDFRQWWQPS        |
| >6.135       | Mosd21 | 21         | FSWSMVMPWPTA        |

The number of the specific phage clone from which the sequence was isolated is specified with the name of the corresponding amino acid sequence of the peptide, which is likewise presented in the form of a one-letter code, and also the corresponding SEQ ID NO:.

FIG. 1: For ELISA experiments, biotinylated, D-enantiomeric Aβ$_{1-42}$ monomers and a mixture of biotinylated D-enantiomeric Aβ$_{1-42}$ oligomers and fibrils were immobilized in respective concentrations of 320 nM on streptavidin-coated 96-well microtiter plates. In order to be able to ensure a correct evaluation of the following monoclonal phage ELISA experiments, the efficiency of the immobilization was tested by means of an Aβ$_{1-42}$-specific antibody (6E10). The absorption at 450 nm was measured and is plotted on the Y-axis. Both Aβ$_{1-42}$ monomers and a mixture of Aβ$_{1-42}$ oligomers and fibrils were immobilized on all used plates (A, B, C), which is evident from the increased absorption values compared to the values of the wells in which no Aβ$_{1-42}$ had been immobilized. Aβ$_{1-42}$ oligomers and fibrils had a higher immobilization efficiency than Aβ$_{1-42}$ monomers.

This means, on the one hand, that the immobilization of the different Aβ$_{1-42}$ species was successful. The amount of immobilized Aβ$_{1-42}$, however, differed between the species, so that a normalization of the values for Aβ$_{1-42}$ monomers and Aβ$_{1-42}$ oligomers and fibrils was necessary for the further evaluation of the experiment (FIG. 2).

FIG. 2: Amplified individual phage clones were examined in respect of their binding affinity for immobilized Aβ$_{1-42}$ monomers, Aβ$_{1-42}$ oligomers and fibrils and the streptavidin-coated plastics surface. The absorption at 450 nm was measured. From left to right, the clones have been illustrated in accordance with the order in Table 1 (5.60-6.135), followed by further tested, but not selected clones (6.262-6.85). The values of the Y axis specify the normalized absorption values of the individual phage clones with respect to monomeric Aβ$_{1-42}$ (black), oligomeric Aβ$_{1-42}$ and fibrillar Aβ$_{1-42}$ (dark grey) and the streptavidin-coated plastics surface (light grey, striped). After deduction of the values of the buffer control, the absorption of the wells which had been immobilized with Aβ$_{1-42}$ oligomers and fibrils was normalized to the Aβ$_{1-42}$ content of the Aβ$_{1-42}$ monomer-coated wells on the basis of the differences, presented in FIG. 1, in the immobilization efficiency of the different Aβ$_{1-42}$ species.

It is clear from the absorption values that all tested phages preferably bind to monomeric Aβ$_{1-42}$. All phages had higher values for monomeric Aβ$_{1-42}$ than for Aβ$_{1-42}$ oligomers and fibrils or for the Aβ$_{1-42}$-free plastics surface. It can be concluded from this that, with the competition step in the method applied here, both a higher specificity for monomeric Aβ$_{1-42}$ compared to Aβ$_{1-42}$ oligomers and fibrils was achieved and a reduced enrichment of plastics-, BSA- or streptavidin-binding phages could be attained with the aid of the changing substrate surfaces. Clone 5.60, which contains the peptide sequence of Mosd1, stands out in particular. The clone has not only the highest absorption values for monomeric Aβ$_{1-42}$ of all tested clones, but is additionally characterized by the greatest difference in the absorption values for monomeric Aβ$_{1-42}$ and oligomeric or fibrillar Aβ$_{1-42}$. This is equivalent to a very high specificity for monomeric Aβ$_{1-42}$.

Figure 3:
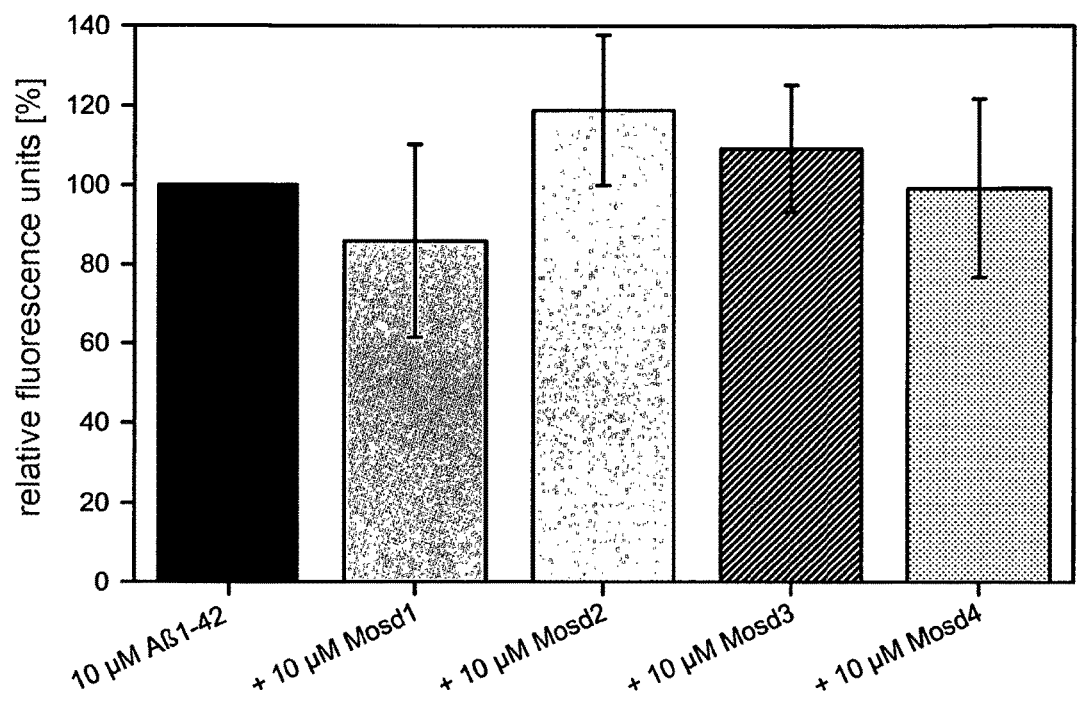
FIG. 3: shows modulation of $A\beta_{1-42}$ aggregation by Mosd peptide-ThT test.

FIG. 3: The average relative fluorescence from seven independently performed ThT experiments with standard deviation is shown. The dye Thioflavin T (ThT) binds to β-pleated sheet structures in the batch and thereupon changes its fluorescence spectrum. During the course of the aggregation of Aβ$_{1-42}$, β-pleated sheet structures form increasingly, which can thus be directly measured by a rise in the ThT fluorescence. The relative fluorescence of a 10 μM Aβ$_{1-42}$ sample (black) served as reference. The time in which the logarithmic rise of the fluorescence signal transitioned into a stationary phase was set to 100%. The use of equimolar concentrations of different peptides influenced the ThT fluorescence and thus aggregation and fibril formation of the Aβ$_{1-42}$ likewise contained in the batch at this moment in time. What are illustrated are the relative fluorescence units for the co-incubation of Aβ$_{1-42}$ with Mosd1 (light grey), Mosd2 (dark grey), Mosd3 (grey, diagonally striped) and Mosd4 (grey, dotted) in equimolar proportions compared to a batch which contained only Aβ$_{1-42}$ (black).

Whereas Mosd2 and 3 increase the ThT fluorescence at the specified moment in time, it is to be assumed that these peptides promote the formation of β-pleated sheet structures. By contrast, Mosd4 has only a very small influence on the formation of β-pleated sheet structures. Mosd1 is able to reduce the relative fluorescence, which is the measure for the proportion of β-pleated sheet structures in the sample. Since none of the tested peptides has inherent fluorescence in this test, it is to be assumed that the increased fluorescence values are caused exclusively by the formation of fibrillar Aβ, i.e. Aβ that contains β-pleated sheet structures. From this, it can be concluded that Mosd1 reduces the proportion of fibrillar Aβ, where possible by the stabilization of Aβ monomers or the formation of large, ThT-negative aggregates. The peptides Mosd2 and Mosd3, by contrast, appeared to accelerate the fibrillation of A. However, this is not necessarily a result to be considered as negative, since the formation of fibrillar Aβ also means that oligomers, as necessary precursor, have been removed from the equilibrium.

Figure 4:
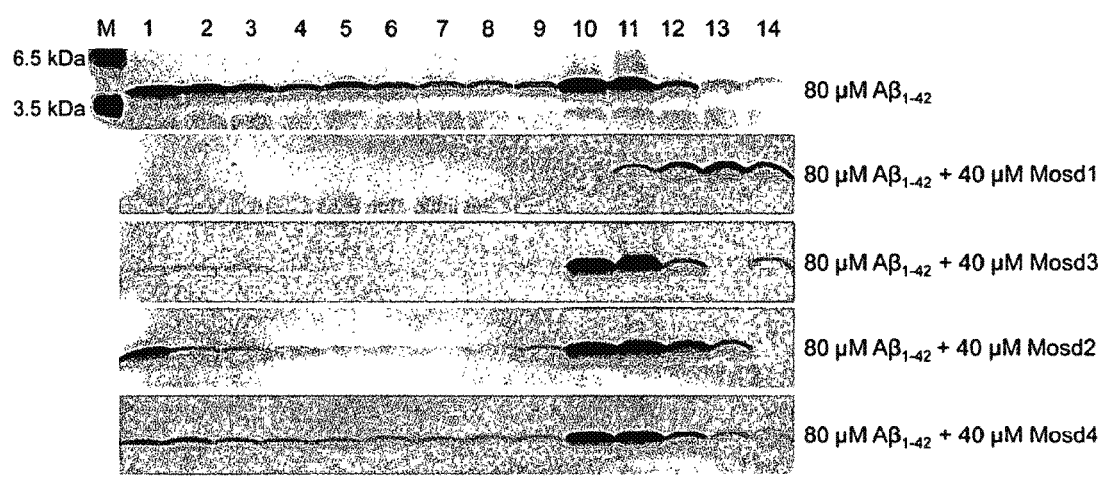
FIG. 4: shows modulation of different $A\beta_{1-42}$ species by Mosd peptides.

FIG. 4: The influence of different Mosd peptides on a diversified mixture of $A\beta_{1-42}$ species of different size was analyzed by means of density gradient centrifugation, fractionation of the gradient by centrifugation, and analysis of the fractions by means of tris-tricine SDS phage and silver staining.

80 μM $A\beta_{1-42}$ were incubated without addition of peptide for 4.5 hours at 600 rpm and 25° C. in order to obtain a broad spectrum of different $A\beta_{1-42}$ species. The batch was then incubated either with or without addition of peptide for a further 40 minutes and was then placed on an iodixanol density gradient. The gradient was then centrifuged, wherein the contents of the sample ($A\beta_{1-42}$ species of different size) diffused within the gradient in accordance with their size and shape. The gradient was fractionated after centrifugation into 15 fractions (1-15), and the first 14 individual fractions were applied to a tris-tricine SDS gel. The contents per fraction were separated electrophoretically. The bands of the denatured proteins ($A\beta_{1-42}$ at 4.5 kDa; see marker (M)) were made visible by means of silver staining. The method does not allow quantitative analysis, but correlates the strength of the signal with the concentration of the proteins, and therefore a stronger signal generally indicates a higher protein concentration.

The influence of the peptides Mosd1-4 in a concentration of 40 μM was examined. The image shows, in the uppermost portion, the distribution of the $A\beta_{1-42}$ species without co-incubation with peptide. A broad spectrum of $A\beta_{1-42}$ species of different size is found in the sample. The peptides Mosd1/2 and 3 increase the proportions of high-molecular $A\beta_{1-42}$ species (fractions 10-14) and reduce, above all, the oligomeric $A\beta_{1-42}$ species (fractions 4-7), which are considered to be toxic.

Figure 5:
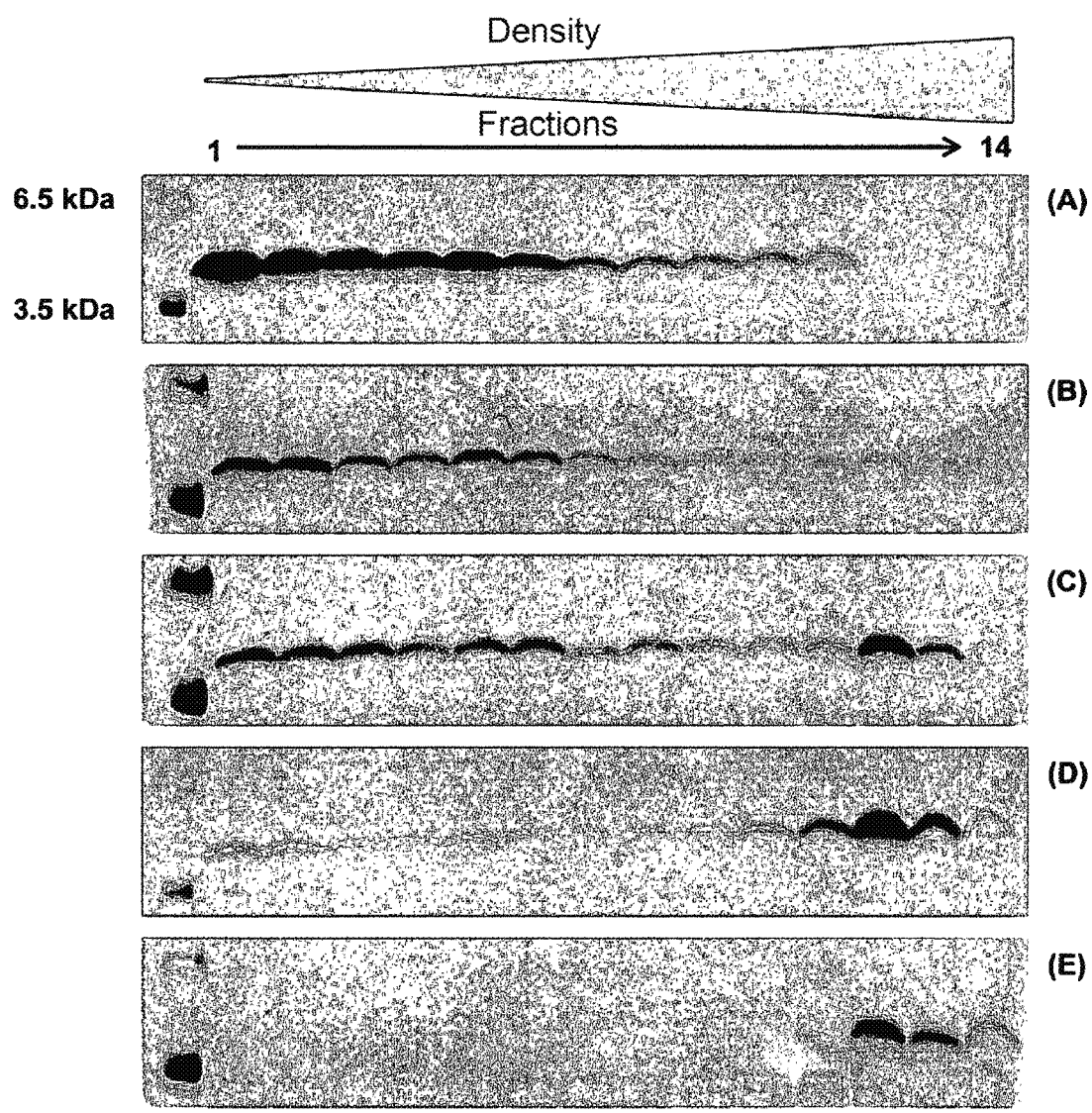
FIG. 5: shows modulation of different $A\beta_{1-42}$ species by Mosd1.

FIG. 5: The influence of different concentrations of Mosd1 on a diversified mixture of $A\beta_{1-42}$ species of different size was analyzed by means of density gradient centrifugation, fractionation of the gradient by centrifugation, and analysis of the fractions by means of tris-tricine SDS phage and silver staining.

80 μM $A\beta_{1-42}$ were incubated without addition of peptide for 4.5 hours at 600 rpm and 25° C. in order to obtain a broad spectrum of different $A\beta_{1-42}$ species. The batch was then incubated either without (A) or with addition of different concentrations of Mosd1 (B=10 μM Mossd1; C=20 μM Mosd1; D=40 μM Mosd1; E=80 μM Mosd1) for a further 40 minutes and was then placed on an iodixanol density gradient. The gradient was then centrifuged, wherein the contents of the sample ($A\beta_{1-42}$ species of different size) diffused within the gradient in accordance with their size and shape. The gradient was fractionated after centrifugation (1-15), and the individual fractions were applied to a tris-tricine SDS gel. The contents per fraction were separated electrophoretically. The bands of the denatured proteins ($A\beta_{1-42}$ at 4.5 kDa; see marker (M)) were made visible by means of silver staining. The method does not allow quantitative analysis, but correlates the strength of the signal with the concentration of the proteins, and therefore a stronger signal generally indicates a higher protein concentration.

The influence of the various concentrations of the peptide Mosd1 were examined. The image shows, in the uppermost portion (A), the distribution of the $A\beta_{1-42}$ species without co-incubation with peptide. A broad spectrum of $A\beta_{1-42}$ species of different size is found in the sample. The modulation of the $A\beta_{1-42}$ species by Mosd1 is concentration-dependent (B-E). Lower concentrations (B & C) of Mosd1 change the composition of the $A\beta_{1-42}$ species only slightly, but reduce the proportion of toxic oligomers (fractions 4-7) compared to the untreated $A\beta_{1-42}$ sample and increase the proportion of high-molecular aggregates. Higher concentrations of Mosd1 (D & E) reduce the proportion of small $A\beta_{1-42}$ species and toxic oligomers considerably and lead to a modulation of the $A\beta_{1-42}$ species towards high-molecular aggregates.

Mosd1 is able to remove any present toxic Aβ oligomers from the pool of different Aβ species and to promote the formation of non-toxic, high-molecular aggregates. This process is concentration-dependent. The use of 20 μM Mosd1 already reduces the signal strength of the oligomer bands and intensifies the signal of the Aβ bands in fractions 11-14 compared to untreated Aβ. Higher concentrations intensify this effect, but also result in a reduction of the signal strength in fractions 1-2, which correspond to monomeric Aβ.

Figure 6:
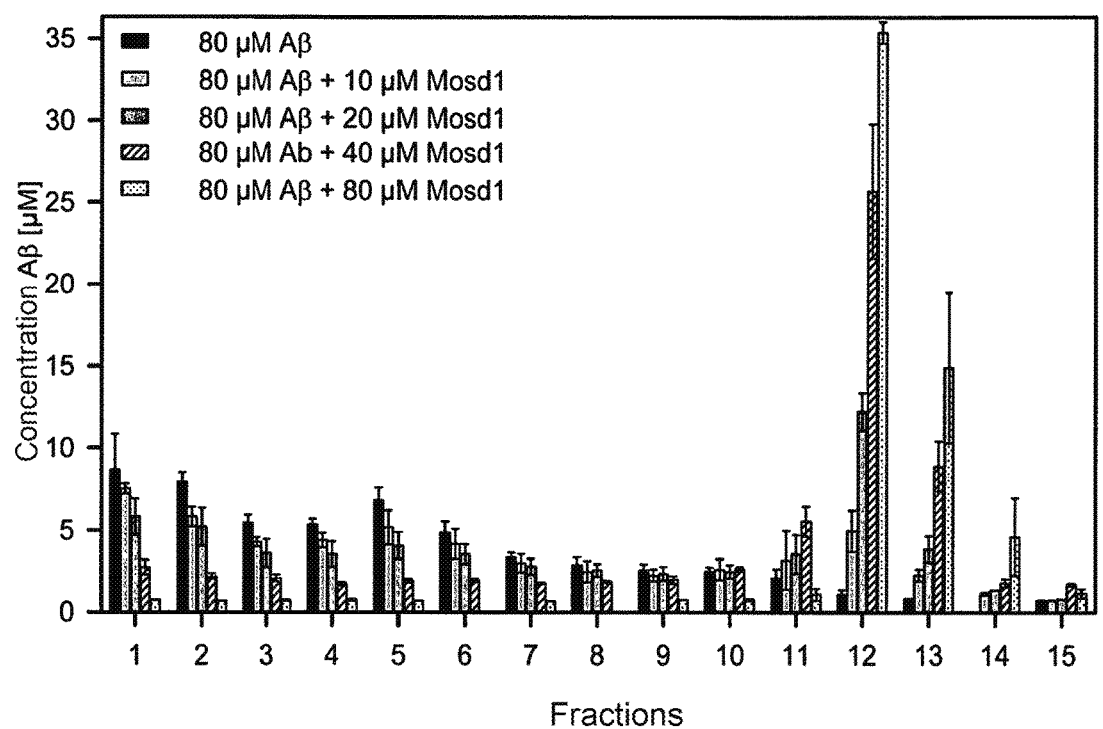
FIG. 6: shows quantification of the modulation of different Aβ$_{1-42}$ species by Mosd1 by means of RP-HPLC.

FIG. 6: The influence of different concentrations of Mosd1 on a diversified mixture of $A\beta_{1-42}$ species of different size was analyzed by means of density gradient centrifugation, fractionation of the gradient by centrifugation, and analysis of the fractions by means of tris-tricine SDS phage and silver staining (FIG. 5). Samples of each fraction from the experiment shown in FIG. 5 were separated and quantified by means of reversed-phase HPLC. For this purpose, the samples were denatured and separated in a mobile phase (30% (v/v) acetonitrile, 0.1% (v/v) TFA in ddH$_2$O) over a Zorbax 300SB-C8 column at increased column temperature (80° C.). For each fraction, samples from 3 experiments performed independently of one another were averaged, and the standard deviation calculated. The results correspond with the results of the gel images of FIG. 5 and allow quantitative analysis of the data. Fraction 15 corresponds to the pellet after density gradient centrifugation and also contains small amounts of $A\beta_{1-42}$.

The quantitative analysis data of the samples by means of RP-HPLC confirm the qualitative assertions from FIG. 5. The concentrations of Aβ in the fractions which contained the toxic oligomers decrease with increasing concentration of Mosd1. The concentration of high-molecular Aβ species (fractions 11-14) also rises at the same time.

Figure 7:
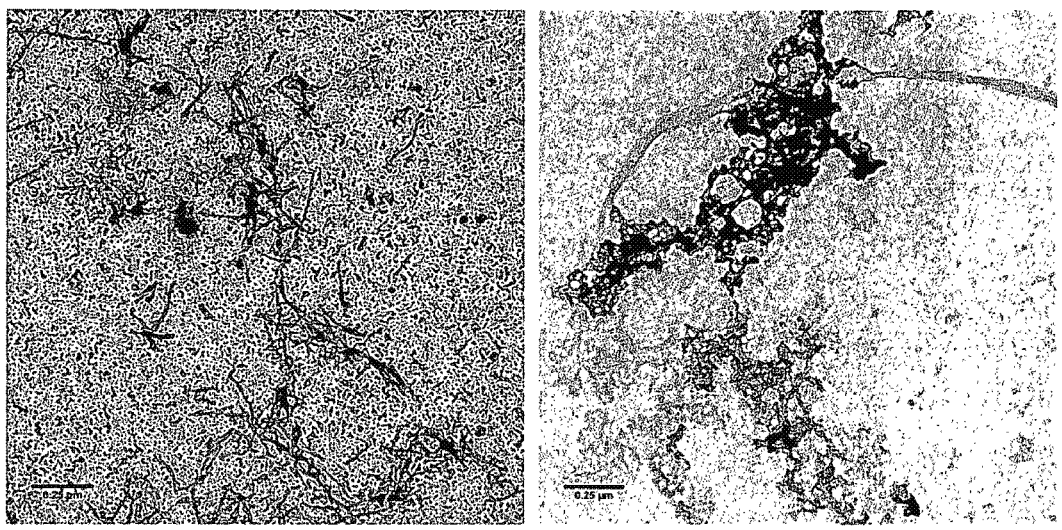
FIG. 7: shows TEM images of 10 μM Aβ$_{1-42}$ incubated with and without 10 μM Mosd1.

FIG. 7: The previous experiments indicate that co-incubation of $A\beta_{1-42}$ with Mosd peptides, in the specific case Mosd1, leads to a modulation of the $A\beta_{1-42}$ aggregation towards high-molecular aggregates. For further analysis, 10 μM $A\beta_{1-42}$ was therefore incubated with and without 10 μM Mosd1 for 24 hours at room temperature and then immobilized on a Formvar/carbon copper grid and stained using uranyl acetate. The subsequent analysis via TEM (120 kV) showed fibrillar structures (left-hand image) if $A\beta_{1-42}$ had been incubated without Mosd1. The co-incubation with Mosd1 led to the formation of large, high-molecular aggregates, which differ considerably from the fibrillar structures (right-hand image). The scale bars correspond to 0.25 μm.

Figure 8:
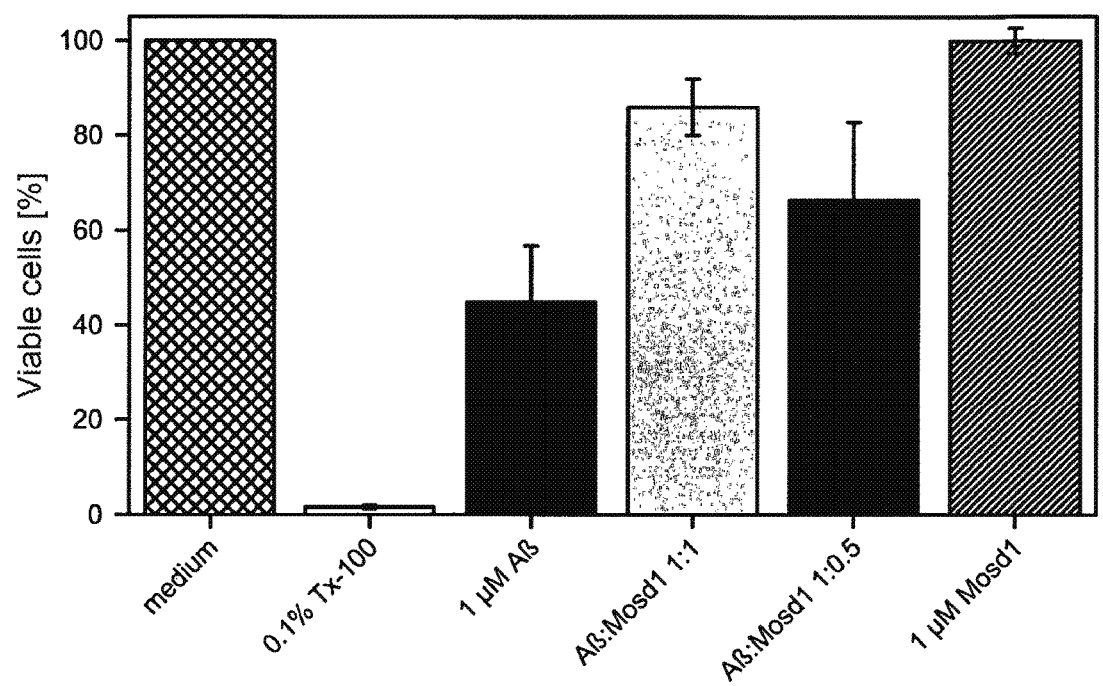
FIG. 8: shows an MTT reduction test: Influence of Mosd1 on Aβ$_{1-42}$-induced cell toxicity.

FIG. 8: The Influence of Aβ$_{1-42}$ on the viability of PC-12 cells was tested. A mixture of different Aβ$_{1-42}$ species (see FIG. 4 for production) was added to PC-12 cells. In addition, as described in FIG. 4, batches of Aβ$_{1-42}$ with different concentrations of Mosd1 were co-incubated, and a batch containing only Mosd1 was tested. The end concentrations per well were 1 μM Aβ$_{1-42}$ and 1 or 0.5 μM Mosd1. The samples were placed in the culture medium of the cells and were incubated over 24 hours with the cells at 37° C. The viability of the cells was then determined on the basis of an MTT test. Here, a metabolic reactant was supplied to the cells, which reactant could be converted by metabolically active cells (living cells). Formazan crystals are the product of this conversion and can be dissolved. The coloration of the medium after solubilization corresponds to the conversion rate of the reactant and therefore the viability of the cells. Untreated cells (medium, white chequered pattern) served as living control, and the proportion of vital cells was defined as 100%. The values of the other batches were normalized to this value. The treatment with 0.1% TritonX-100 served as positive control for cell toxicity (light grey), and the amount of viable cells in this batch was just 1.5%. The mixture of different Aβ$_{1-42}$ species contained, as suspected, also toxic species, and therefore the number of living cells reduced to 45% (black) by incubation of the cells with the Aβ$_{1-42}$ mixture. Mosd1 had no influence on the viability of PC-12 cells. Co-incubation of Aβ$_{1-42}$ and Mosd1, however, reduced the toxicity of Aβ$_{1-42}$ in a concentration-dependent manner (grey (1 μM Mosd1) and dark grey (0.5 μM Mosd1)). 86% and 66% of the cells, respectively, survived if the Aβ$_{1-42}$ mixture was co-incubated with Mosd1 before being added to the cells.

This shows that Mosd1 is able to convert toxic aggregates into high-molecular, non-toxic Aβ$_{1-42}$ species or to disintegrate the toxic Aβ$_{1-42}$ species.

Figure 9:
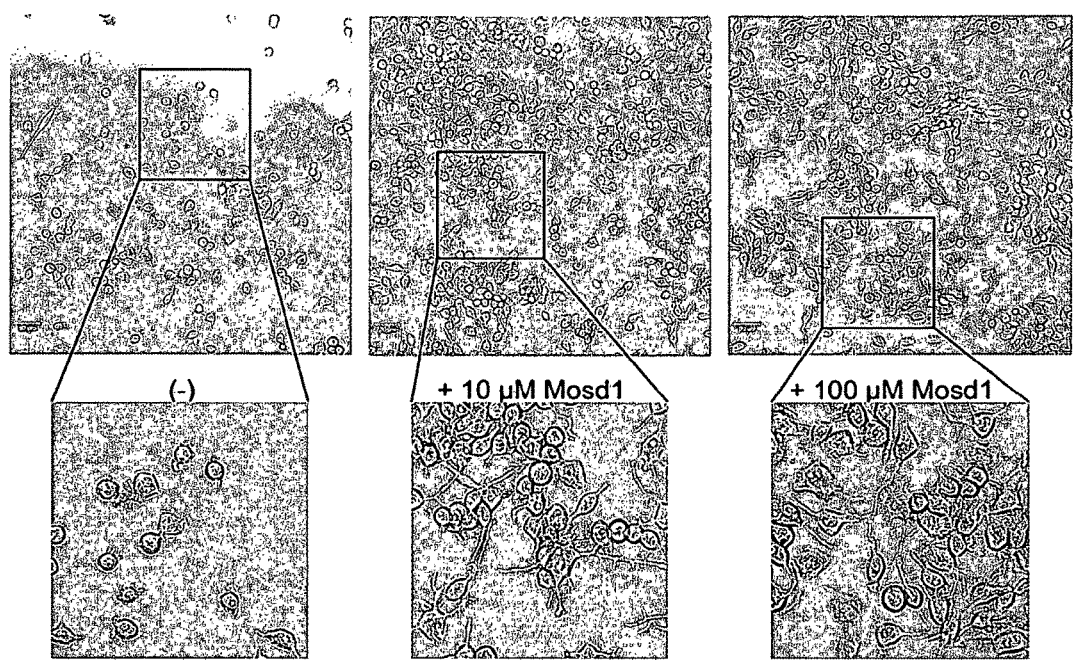
FIG. 9: shows the influence of Mosd1 on APP-expressing cells.

FIG. 9: The murine neuroblastoma cell line Neuro-2a serves as a model for neuronal cells and is thus suitable for analyzing the symptoms of AD. The stable transfection of Neuro-2a cells with human APP695 additionally allows a model which produces human APP (amyloid precursor protein) and all processing products thereof, including the toxic Aβ$_{1-42}$, produced in the cell itself. In this way, the influence of naturally occurring Aβ$_{1-42}$ species can be examined directly in neuronal cells. In the experiment, Neuro-2a cells were cultivated without APP parallel to those with the APP transfection. The production of APP and processing products thereof shows rounded and individualized cells, which have only little contact with one another (left-hand image). By incubation with 10 μM or 100 μM Mosd1, however, this pathological phenotype can be reversed, and the cells develop in accordance with the physiological phenotype corresponding to wild-type Neuro-2a cells. This means that the cell number increases and the cells accumulate, have a polygonal shape and form numerous cell contact points and spurs (middle and right-hand image).

This shows that Mosd1 is not only capable of breaking down or converting toxic Aβ$_{1-42}$ species, but can also prevent the formation of toxic species.

The results shown for Mosd1 can also be expected for the peptides and polymers of SEQ ID NO: 2-21. The results shown in the practical examples are therefore obtained analogously also for the peptides according to all SEQ ID NO: 1-21 and generally for peptides obtained with a method according to certain embodiments of the invention, that is to say the modified mirror-image phage display.

It should be noted at this juncture that the applied mirror-image phage display can be performed in exactly the other direction, that is to say for identification of ligands at A beta oligomers, by using A beta oligomers as bait and A beta monomers and/or A beta fibrils as competitors. In addition, the mirror-image phage display according to certain embodiments of the invention can of course also be applied for other bait-competitor pairs.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A peptide specifically binding an amyloid beta species, said peptide comprising at least one amino acid sequence selected from the group consisting of SEQ ID NO: 1, SEQ ID NO: 2, SEQ ID NO: 3, SEQ ID 4, SEQ ID NO: 5, SEQ ID NO: 6, SEQ ID NO: 7, SEQ ID NO: 8, SEQ ID NO: 9, SEQ ID NO. 10, SEQ ID NO. 11, SEQ ID NO. 12, SEQ ID NO. 13, SEQ ID NO: 14, SEQ ID NO: 15, SEQ ID NO: 16, SEQ ID NO: 17, SEQ ID NO: 18, SEQ ID NO: 19, SEQ ID NO: 20, and/or SEQ ID NO: 21 and polymers of SEQ ID NO: 1, SEQ ID NO: 2, SEQ ID NO: 3, SEQ ID 4, SEQ ID NO: 5, SEQ ID NO: 6, SEQ ID NO: 7, SEQ ID NO: 8, SEQ ID NO: 9, SEQ ID NO. 10, SEQ ID NO. 11, SEQ ID NO. 12, SEQ ID NO. 13, SEQ ID NO: 14, SEQ ID NO: 15, SEQ ID NO: 16, SEQ ID NO: 17, SEQ ID NO: 18, SEQ ID NO: 19, SEQ ID NO: 20 and/or SEQ ID NO: 21.

2. The peptide according to claim 1,
wherein the peptide consists substantially of D-amino acids.

3. The peptide according to claim 1,
wherein the peptide is present in cyclized form.

4. A kit comprising the peptide of claim 1.

5. A composition comprising the peptide of claim 1.

6. The peptide of claim 1, wherein the peptide specifically binds to A beta monomers.

7. The peptide according to claim 1, wherein the peptide comprises the amino acid sequence of SEQ ID NO: 1.

8. The peptide according to claim 1, wherein the peptide comprises the amino acid sequence of SEQ ID NO: 2.

9. The peptide according to claim 1, wherein the peptide comprises the amino acid sequence of SEQ ID NO: 3.

10. A method for the specific identification and quantitative and/or qualitative determination of amyloid beta monomers, amyloid beta fibrils and/or amyloid beta oligomers, comprising contacting the peptide of claim 1 with amyloid beta monomers, amyloid beta fibrils and/or amyloid beta oligomers.

11. A method for inhibiting the formation of amyloid beta oligomers and/or amyloid beta peptide aggregates, comprising binding the peptide of claim 1, to amyloid beta monomers.

12. A method of treating Alzheimer's disease in a subject, comprising administering a therapeutically effective amount of the peptide of claim 1 to the subject.

13. The method according to claim 12, wherein the peptide comprises the amino acid sequence of SEQ ID NO: 1.

14. The method according to claim 12, wherein the peptide comprises the amino acid sequence of SEQ ID NO: 2.

15. The method according to claim 12, wherein the peptide comprises the amino acid sequence of SEQ ID NO: 3.

* * * * *

SEQUENCE LISTING

<160> NUMBER OF SEQ ID NOS: 21

<210> SEQ ID NO 1
<211> LENGTH: 12
<212> TYPE: PRT
<213> ORGANISM: Artificial Sequence
<220> FEATURE:
<223> OTHER INFORMATION: D-Peptide, Mosd1

<400> SEQUENCE: 1

Tyr Ser Tyr Leu Thr Ser Tyr His Met Val Trp Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: D-Peptide, Mosd2

<400> SEQUENCE: 2

His Thr Trp Thr Thr Tyr Asp Tyr Val Trp Arg Leu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: D-Peptide, Mosd3

<400> SEQUENCE: 3

Gly Thr Met Leu Lys Phe Ser Gly Met Asn Leu Thr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: D-Peptide, Mosd4

<400> SEQUENCE: 4

His Asn Trp Phe Tyr Trp Thr Thr Glu Pro Tyr Asp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: D-Peptide, Mosd5

<400> SEQUENCE: 5

His Asn Trp Ser Trp Glu Trp Trp Tyr Asn Pro Asn
1               5                   10

<210> SEQ ID NO 6
<211> LENGTH: 12
<212> TYPE: PRT
<213> ORGANISM: Artificial Sequence
<220> FEATURE:
<223> OTHER INFORMATION: D-Peptide, Mosd6

<400> SEQUENCE: 6

Ser Thr Leu His Phe Tyr Thr Ala Phe Leu Asn Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: D-Peptide, Mosd7

<400> SEQUENCE: 7

Phe Ser His Ser His His Thr Trp Phe Thr Trp Asn

```
<210> SEQ ID NO 8
<211> LENGTH: 12
<212> TYPE: PRT
<213> ORGANISM: Artificial Sequence
<220> FEATURE:
<223> OTHER INFORMATION: D-Peptide, Mosd8

<400> SEQUENCE: 8

His Phe Trp Ser Trp Thr Ser Leu Ser Met Thr Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: D-Peptide, Mosd9

<400> SEQUENCE: 9

His Leu Ser Trp Tyr Trp Glu Lys Tyr Leu Thr Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: D-Peptide, Mosd10

<400> SEQUENCE: 10

His Thr Trp Thr His Trp Phe Ser Trp Asn Val Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: D-Peptide, Mosd11

<400> SEQUENCE: 11

Leu Ser Met Asn Ile Thr Thr Val His Arg Trp His
1               5                   10

<210> SEQ ID NO 12
<211> LENGTH: 12
<212> TYPE: PRT
<213> ORGANISM: Artificial Sequence
<220> FEATURE:
<223> OTHER INFORMATION: D-Peptide, Mosd12

<400> SEQUENCE: 12

Val His Trp Asp Phe Arg Gln Trp Trp Gln Gln Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: D-Peptide, Mosd13

<400> SEQUENCE: 13

Tyr Ser Phe His Phe Glu Met Asn Met Gly Asn Tyr
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: D-Peptide, Mosd14

<400> SEQUENCE: 14

Glu His Trp Asp Phe Gly Gln Trp Trp Gln Gln Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: D-Peptide, Mosd15

<400> SEQUENCE: 15

Gly Gln Trp Asp Phe Arg Gln Trp Trp Gln Pro Cys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: D-Peptide, Mosd16

<400> SEQUENCE: 16

Asp Trp Ser Ser Arg Val Tyr Arg Asp Pro Gln Thr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: D-Peptide, Mosd17

<400> SEQUENCE: 17

Glu Arg Ser Gln Trp Gly His Arg Asp Pro Gln Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: D-Peptide, Mosd18

<400> SEQUENCE: 18

Asp Arg Ser Lys Gly Asp His Arg Ile Thr Gln Met
1               5                   10

<210> SEQ ID NO 19
<211> LENGTH: 12
<212> TYPE: PRT
<213> ORGANISM: Artificial Sequence
<220> FEATURE:
<223> OTHER INFORMATION: D-Peptide, Mosd19

<400> SEQUENCE: 19

Asp Leu Arg Phe Ser Ser Leu Trp Lys Leu Ser His
1               5                   10

```
<210> SEQ ID NO 20
<211> LENGTH: 12
<212> TYPE: PRT
<213> ORGANISM: Artificial Sequence
<220> FEATURE:
<223> OTHER INFORMATION: D-Peptide, Mosd20

<400> SEQUENCE: 20

Val His Trp Asp Phe Arg Gln Trp Trp Gln Pro Ser
1               5                   10

<210> SEQ ID NO 21
<211> LENGTH: 12
<212> TYPE: PRT
<213> ORGANISM: Artifical Sequence
<220> FEATURE:
<223> OTHER INFORMATION: D-Peptide, Mosd21

<400> SEQUENCE: 21

Phe Ser Trp Ser Met Val Met Pro Trp Pro Thr Ala
1               5                   10
```